United States Patent
Acemoglu

[19]

[11] Patent Number: 5,849,859

[45] Date of Patent: Dec. 15, 1998

[54] POLYESTERS

[75] Inventor: Murat Acemoglu, Basel, Switzerland

[73] Assignee: Novartis AG, Basel, Switzerland

[21] Appl. No.: 307,754

[22] PCT Filed: Mar. 23, 1993

[86] PCT No.: PCT/EP93/00699

§ 371 Date: Sep. 26, 1994

§ 102(e) Date: Sep. 26, 1994

[87] PCT Pub. No.: WO93/20126

PCT Pub. Date: Oct. 14, 1993

[30] Foreign Application Priority Data

Mar. 27, 1992 [GB] United Kingdom ............... 9206736

[51] Int. Cl.[6] .................................................. C08G 63/00
[52] U.S. Cl. .................. 528/271; 528/272; 528/295.5; 528/302; 424/278.1; 424/279.1; 424/280.1; 114/2; 114/23; 114/54
[58] Field of Search ........................... 528/271, 272, 528/295.5, 302; 424/278.1, 279.1, 280.1; 514/2, 23, 54

[56] References Cited

U.S. PATENT DOCUMENTS

| | | | |
|---|---|---|---|
| 2,789,968 | 4/1957 | Reynolds | 549/228 |
| 4,101,533 | 7/1978 | Hafferty et al. | 510/491 |
| 4,356,166 | 10/1982 | Peterson et al. | 424/29 |
| 4,968,611 | 11/1990 | Traussnig et al. | 435/135 |
| 5,188,837 | 2/1993 | Domb | 424/450 |

FOREIGN PATENT DOCUMENTS

| | | |
|---|---|---|
| 0502194 | 9/1992 | European Pat. Off. . |
| 0514790 | 11/1992 | European Pat. Off. . |
| 2551072 | 3/1985 | France . |
| 1921866 | 11/1970 | Germany . |

OTHER PUBLICATIONS

M. Takanashi, et al. Die Makromolekulare Chemie, vol. 183, No. 9, Sep. 1982.

*Primary Examiner*—Duc Truong
*Attorney, Agent, or Firm*—Gabriel Lopez

[57] ABSTRACT

A biodegradable and biocompatible polyester comprising ($C_{3-10}$) alkylene carbonic acid ester units, each alkylene group being a $C_3$-alkylene group having 1 oxy substituent or a ($C_{4-10}$) alkylene group having 2–8 oxy substituents, each of the oxy substituents occurring individually as a hydroxyl group or as a derivatized hydroxyl group comprising an ester or an ortho ester or an acetal residue.

The polyesters may be used as matrices for the sustained release of pharmacologically active compounds, e.g. peptides or proteins, in the form of microparticles or implants.

30 Claims, 4 Drawing Sheets

Degradation in Vitro (PBS; ph 7.4) and in Vivo (Rats; s.c.) of the Polymer Having the Monomer Units 4c (means +/-sem)

Degradation in Vitro (PBS; ph 7.4) and in Vivo (Rats; s.c.) of the Polymer Having the Monomer Units 11c (means +/−sem)

In Vitro Degradation and Drug Release
From Polymer Implants Having Monomer Unit 4c

POLYESTERS

The invention relates to biodegradable and biocompatible polyesters and to pharmaceutical compositions containing them.

The function of the polyesters in the pharmaceutical compositions is to control the rate of the release of pharmacologically active compounds from the compositions and the duration of the activity in the animal body to which the compositions are administered.

Although we do not wish to be bound by any theory, it is believed that when administered to the body the polyesters can initially screen off the pharmacologically active compounds from the aqueous media, present in the body, whereafter due to biodegradation of the polyesters or to diffusion of the drug compounds through the polyesters, the drug releases and becomes medically active. This may be an interesting mechanism e.g. when the polyesters are water-insoluble.

In the compositions the drug compound may also be chemically bound to the polyesters, whereafter due to biodegradation of the polyester molecule part, the drug releases from the compositions. This may be an interesting mechanism e.g. when the polyesters are water-soluble and the polyester-drug compound combination functions as a water-soluble pro-drug.

Dependent on the type of release mechanism the drug compound can be set free e.g. within one or more hours or days if chemically bound to polyesters or within one or more days, weeks or months if screened off by the polyesters.

The invention provides biodegradable, biocompatible polyesters comprising ($C_{3-10}$) alkylene carbonic acid ester units, each alkylene group being a $C_3$-alkylene group having 1 oxy substituent or a ($C_{4-10}$) alkylene group having 2–8 oxy substituents, each of the oxy substituents occurring independently as a hydroxyl group, or as a moiety independently comprising an ester or an ortho ester or an acetal group.

Thus the polymers may contain e.g. mixtures of different oxy substitutents. Preferably the oxy substituents are the same. Representative compounds may contain however a hydroxyl group and an oxy substituent, e.g. up to 30 or 20% hydroxyl groups.

The polyesters of carbonic acid are in principle biodegradable since their backbone chains contain carbonic acid esters bonds —O—C(=O)—O— which are hydrolysable in the human body's aqueous media, at suitable pH, e.g. in the presence of hydrolytic enzymes, e.g. esterases. Polyesters containing carbonic acid ester groups are generally known as rather stable polymeric materials. Exceptions reported so far are poly(ethylene carbonate)s, which decompose within approximately 2–4 weeks in vivo.

The next higher homologue, namely poly(trimethylenecarbonate), is not completely decomposed in vivo even after 6 months. Both poly(ethylenecarbonate) and poly(trimethylene carbonate) are polymers in which the alkylene group is unsubstituted.

The polyesters of the invention comprise preferably $C_3$-alkylene groups or ($C_{4-10}$) alkylene groups situated between the carbonic acid ester groups, each having 2 terminal —CH$_2$— groups. ($C_{4-10}$)alkylene groups have a ($C_{2-8}$) alkylene central part carrying at least 2 and at most 8 hydroxyl groups in free form or in a form in which at least one of them is a derivatized hydroxyl group, comprising an ester or an orthoester or an acetal residue. A $C_3$-alkylene group has a methylene central part, carrying 1 hydroxyl or derivatized hydroxyl group. Polyesters having such $C_3$-alkylene or ($C_{4-10}$) alkylene units between the carbonic acid ester groups are novel.

They are in principle biodegradable, many quickly, others slowly, depending on their structural type. Preferred are those which biodegrade within 1–90 days.

Preferably all the carbon atoms belonging to the ($C_{2-8}$) alkylene central part of the ($C_{4-10}$) alkylene groups are oxysubstituted.

The polyesters of the invention can be prepared by methods known per se, e.g. by reacting:

a diol with phosgene
1. French Patent 905,141 (1945)
2. U.S. Pat. No. 2,999,844 (1961)
3. German patents 117,625; 118-536-7;

a diol with a bis(chloroformate)
4. German patent 857,948 (1952)

a diol with a dialkyl carbonate
5. W. H. Carothers and F. J. Van Natta, J. Amer. Chem. Soc. 314, 52, (1930)
6. J. H. Hill and W. H. Carothers, J. Amer. Chem. Soc. 5031, 55, (1933)
7. S. Sarel, L. A. Pohoryles and R. Ben-Shoshnan, J. Org. Chem. 1873, 24, 1959.

a diol with urea
8. EP 0,057,825 A1 and by polycondensation of bis (alkyl carbonates)
9. U.S. Pat. No. 2,789,968 (1957)

ring opening polymerization of cyclic carbonates: see 5. and 6.

ring opening polymerization of spiroortho carbonates
10. S. Sakai, T. Fujinami and S. Sakurai, J. Polym. Sci. Polym. Lett. Ed. 631, 11, (1973)
11. T. Endo and W. J. Bailey, J. Polym. Sci., Polym. Chem. Ed., 2525, 13, (1975)

copolymerization of epoxides
12. S. Inoue, H. Koinuma and T. Tsuruta, J. Polym. Sci. B, 287, 7, (1969)
13. U.S. Pat. No. 3,900,424 (Inoue et al).
14. U.S. Pat. No. 3,953,383 (Inoue et al).
15. U.S. Pat. No. 4,665,136 (Santangelo et al).

The invention thus also provides a process for the production of a polyester of the invention by reacting a bifunctional reactive carbonic acid ester derivative with a bifunctional reactive sugar alcohol or glycerol having one or more protected secondary hydroxyl groups and 2 free primary hydroxyl groups.

Depending on the type of the production process the polyesters may be prepared having a molecular weight from several hundreds to more than a million daltons (Da).

Generally diol or bis (alkyl) carbonate polycondensations give linear polyester chains having lower molecular weights of 1000–50,000 Daltons.

Anionic ring opening polymerizations of cyclic carbonates generally lead to products having higher molecular weights, e.g. up to more than 100,000 Daltons:
16. H. Keul, R. Baecher and H. Hoecker, Makromol. Chem. 187, 2579 (1986)

Cationic ring opening polymerization
17. H. R. Kricheldorf et al., Makromol. Chem. 188, 2453, (1987)

and also polymerizations in the presence of complexing catalysts
18. H. R. Kricheldorf et al., Makromol. Chem. 192, 2391, (1991)

however lead to polycarbonates of lower molecular weight. Polyesters having the highest molecular weights of e.g. more than 1,000,000 Daltons may be obtained by copolymerization of epoxides with carbon dioxide (12–15). When prepared according to the same production processes, the polyesters of the invention have basically molecular weights of the same ranges. Preferred are polyesters having 5–1000, e.g. up to 500 backbone alkylene carbonic acid ester units.

Typical polyesters have Mw from about 5000 to about 25,000 Da. Typical Mw/Mn are from 1.2–1.9.

As indicated above, for the production of the polyesters a diol may be used. Since preferably all the backbone chain carbon atoms are oxy substituted in the polyesters of the invention, preferably a sugar alcohol (reduced sugar, particularly reduced monosaccharides, e.g. threitol) or glycerol is chosen of which the secondary hydroxy groups may be protected.

A preferred process feature is thus using bifunctionally reactive sugar alcohols or glycerol having one or more additional, protected, secondary hydroxyl groups. In case of glycerol 2-benzyloxy-1,3-propandiol can be used as a known starting compound.

Except where otherwise mentioned, carbon containing moieties preferably contain up to 12 carbon atoms, and if they are substituted contain one substituent or conveniently no substituent.

Protection in sugar alcohols may occur by methods known per se, e.g. by the pre-protection of the primary terminal hydroxyl groups, e.g. by converting them into benzoic acid ester groups, by converting the secondary hydroxyl groups to e.g. acetals or hemiacetals e.g. with acetone giving rise to O-isopropylidene residues and by splitting off the benzoic acid ester groups with e.g. methanol in the presence of sodium methylate. The thus obtained sugar alcohols have two free terminal primary hydroxyl groups and protected secondary hydroxyl groups and can be used as diol starting compounds for the production of the polyesters of the invention.

The obtained polyesters, having protected secondary hydroxyl groups in the form of an acetal and/or a hemi-acetal residue, are compounds according to the invention.

The hemi-acetal or acetal groups may be removed by methods known per se, e.g. by water and trifluoroacetic acid, leading to polyesters having free secondary hydroxyl groups, which are also compounds of the invention.

A further, optional, process feature for the preparation of compounds of the invention other than hemi-acetals or acetals is thus deprotecting the secondary hydroxyl groups in the formed polyesters.

A derivatization of secondary hydroxyl groups is broadly described in the chemical literature, e.g. in 19. Houben-Weyl, "Methoden der Organischen Chemie", Bd. VIII (1952), Pages 75 and 503.
20. Houben-Weyl, "Methoden der Organischen Chemie", Erw. Bd. E4, (1983), Page 66.
21. Harrison, "Compendium of Organic Synthetic Methods", Vols. I–IV, (1971–1980).
22. S. G. Wilkinson in "Comprehensive Organic Chemistry", D. Barton and W. D. Ollis, Eds., Vol. I, p. 579, (1979).

For a derivatization to carboxylic ester residues, the polyesters having free hydroxylic groups are preferably dissolved or suspended in an inert, aprotic solvent e.g. in tetrahydrofuran, methylene chloride, toluene or dimethylformamide and reacted in the presence of a catalyst, e.g. a tertiary amine, with an active carboxylic acid derivative.

Active carboxylic acid derivatives are e.g. carboxylic acid anhydrides and carboxylic acid chlorides. These derivatives may be obtained by reacting the carboxyclic acid with an activation reagent and can often be brought into contact with the hydroxyl groups when formed in situ. Reaction with ketenes leads also to the introduction of carboxylic acid ester residues.

Examples of activation reagents are
dicyclohexyl carbodiimide
   23. A Hassner et al., Tetrahedron Lett. 4475 (1978)
di-(N-succinimidyl)-carbonate
   24. a) H. Ogura et al., Tetrahedron Lett. 4745 (1979)
      b) T. Tokubo et al., J. Amer. Chem. Soc. 109, 606 (1987)
bis-(2-oxo-3-oxazolidinyl)-phosphinic acid chloride
   25. a) J. Diago-Meseguer et al., Synthesis 547 (1980)
      b) E. J. Corey et al., J. Amer. Chem. Soc. 104, 6818 (1982)
1,1'-carbonyl-diimidazole and further diazoles, as well as thionyl-diazoles
   26. H. A. Staab, Angew. Chem. 74, 407 (1062)

Polyesters according to the invention are those in which the carboxylic acid ester residues comprise those of formic acid and/or saturated or unsaturated ($C_{2-20}$) fatty acids, e.g. of lauric acid, oleic acid or stearic acid. Conveniently the carboxylic acid residues are unsubstituted.

Further polyesters according to the invention include those in which the carboxylic ester residues comprise moieties of a hydroxy carboxylic acid, e.g. those of lactoyl or glycoyl or of polylactoyl, polylactoyl-co-glycoyl or polyglycoyl, such with the pre-fix "poly" however not having chain lengths enabling the polyester to form a hydrogel in an aqueous medium, to exclude hydrogels described in the EP 92918.

Based upon the methods in the literature and choosing the appropriate reagents, polyesters may be obtained and are in the scope of the invention, in which the derivatized hydroxyl groups comprise substituted carboxylic acid ester residues, e.g. oxo carboxylic acid ester residues, or dicarboxylic acid ester residues.

For a derivatization to carbonic acid ester residues the polyesters having free hydroxyl groups are reacted with active carbonic acid derivatives, preferably with chloroformic acid esters or pyrocarbonates (=carbonic acid anhydrides).

The polyesters according to the invention thus also comprise those in which the derivatized hydroxyl groups are carbonic acid ester residues, e.g. those containing hydroxy carboxylic acid ester residues or being cyclic carbonate residues.

Further polyesters according to the invention are such having carbonic acid ester residues, e.g. comprising those containing a steroid alcohol, like cholesterol or a ($C_{1-20}$) alkanol residue.

Additionally polyesters according to the invention are those in which the derivatized hydroxyl groups comprise such carbonic acid ester residues which contain carbamic acid or a derivative thereof. Carbamates of hydroxy compounds are generally made e.g. by their conversion with isocyanates or with carbamoyl chlorides.

The residues may also comprise ortho ester residues, e.g. those of an ortho carboxylic acid ester or an ortho carbonic acid ester, which are acid sensitive and thus increase the biodegradability of the polyesters of the invention.

Polyesters according to the invention may be those in which the derivatized hydroxyl groups comprise those of an amino acid or peptide. The amino acid residue can be present as a part of a carboxylic acid ester residue or as a part of a carbonic acid ester residue, if the amino acid contains hydroxyl, e.g. serine, or as a part of a carbamic acid ester residue.

If the amino acid residue is a carboxylic acid ester or a carbonic acid ester derivative, the amino group may be present in free condition, in a protected form or in a salt form.

The polyesters of the invention may e.g. thus be obtained by reacting the secondary free hydroxyl groups or a reactive derivative thereof with mono- or bifunctional carboxylic acid or carbonic acid derivatives.

The terminal groups of the polyesters of the invention are free hydroxyl and/or esterified hydroxyl groups, depending on the preparation method applied. If an anionic ring opening polycondensation is applied, the starter molecule will be incorporated as a terminal group into each polyester chain.

In the polycondensation examples described hereinafter products are obtained having ethoxycarbonyloxy and/or hydroxyl terminal groups.

Terminal esterified hydroxyl groups are e.g. those which have been formed during the preparation step of the polyester back bone chain, e.g. ethoxycarbonyloxy.

Other terminal esterified groups are those obtained from terminal hydroxyl groups during the esterification step of the secondary hydroxyl groups.

Further derivatization of terminal groups may be obtained by selectively reacting terminal hydroxyl groups with e.g. esterification agents or by splitting the polycarbonate chain by transesterification reactions, before splitting off the groups protecting the secondary hydroxyl groups, e.g. acetal residues. In such manner lipophilic residues, like stearoyl groups can be introduced as terminal groups. After splitting off the protecting groups amphiphilic products are obtained characterized by hydrophilic secondary hydroxyl groups and lipophilic terminal residues.

The invention thus additionally provides a process for the production of the polyesters of the invention by
a) reacting a bifunctionally reactive carbonic acid ester derivative with a bifunctionally reactive sugar alcohol or glycerol having one or more protected secondary hydroxyl groups and 2 free primary hydroxyl groups, and optionally,
b) for the production of end-group modified polyesters treating the polyester obtained with an esterification or transesterification reagent and, optionally,
c) for the production of polyesters having free secondary hydroxyl groups, deprotecting the secondary hydroxyl groups in the formed polyester, and, optionally,
d) for the production of esters and orthoesters reacting the secondary free hydroxyl groups with mono or bifunctional carboxylic acid or carbonic acid derivatives.

A typical sugar alcohol has e.g. 4–6 carbon atoms, e.g. threitol or mannitol.

The invention further provides a process for the production of polyesters having an acetal residue by choosing for reaction step a) a bifunctionally reactive sugar alcohol having secondary hydroxyl groups protected by an acetal residue.

The polyesters comprise generally alkylene carbonic acid ester units in homopolyester arrangement, although other configurations may be contemplated.

If their alkylene parts contain free hydroxyl groups as well as derivatized hydroxyl residues, their distribution over the alkylene units of the polymer chain in preferably random. The arrangement is then that of a randomized homopolycarbonate.

Preferably the number of alkylene carbonic acid ester backbones units, also when partially or completely derivatized, is 5 to 1000.

The novel alkylene carbonate units can however also be chemically combined with known ester units e.g. also of the carbonic acid ester type and/or of the hydroxy carboxylic ester type to form a polymer chain. If so, the novel alkylene carbonate units form with the known ester units a polycarbonate or a polyester chain having a randomized co-polyester or a block-co-polyester arrangement respectively.

Preferably the number of ester units, inclusive the known ester units, is 5 to 1000, e.g. 5 to 500.

The polyesters of the invention are preferably prepared from sugar alcohols, particularly those of natural sources, which are optically active and thus are stereomeric isomers. Their chiral, asymmetric centres are the carbon atoms to which secondary hydroxyl groups are bound. When the sugar alcohol molecules are converted to polyesters and the hydroxyl groups are derivatized, no significant change in the asymmetric arrangement takes place, although the type of derivatization may influence the size of optical rotation of each asymmetric carbon atom involved.

This means that the polyesters will have corresponding asymmetric arrangements.

The sugar alcohols can be used in any stereomeric enantiomer form, in racemate form, in meso form or in mixtures in which one of the enantiomers preponderates over the other.

In the Examples hereinafter it is indicated, which optically active sugar alcohols (D,L,DL-isomer) were used for the polyester synthesis.

The polyesters of the invention contain cleavable bonds and are of a type, biodegradable in neutral or acidic or basic media. Although in fact all the different residue types mentioned can be present together in one polyester molecule, for reasons of a simpler production method preferred polyesters, if derivatized, those are taken which contain only one type of residue. Further, preferably polyesters are taken which have only one ester bond type, i.e. the carbonate bond, in their backbones.

Preferred are thus polyesters in homopolyester arrangement, especially in randomized homopolycarbonate arrangement.

The amino acid and the steroid alcohol residues can be the active part of a drug compound.

The polyesters thus also include such in which the derivatized hydroxyl groups comprise drug compound residues, e.g. further those of a peptide or a protein. The polyester structures have then a pro-drug character. They can be used in pharmaceutical compositions.

Water soluble polyesters, e.g. those of Examples 4–6, are preferred for pro-drug formation, enhancing drug solubilization and/or releasing drugs by cleavage of a labile bond.

If the terminal groups are modified, e.g. by stearoylation, the polyester is capable of being incorporated into liposomes by lipophile—lipophile interaction in an aqueous medium, leaving the main hydrophilic polymer chain in the outer sphere of the liposome.

This may result in an enhanced circulation period in the blood, similar to that obtained for polyethylene glycol (U.S. Pat. No. 5,013,556) or ganglioside GM1-modified (U.S. Pat. No. 4,837,028) liposomes.

However, the pharmaceutical compositions of the invention preferably contain a polyester of the invention mixed with a drug compound, especially in such manner that the polyester is a solid matrix for the drug compound e.g. in the form of a microparticle or an implant. The polyesters however can also be used as a capsule wall material, e.g. for normal size or microcapsules.

In WO 89/05664 polyesters have been described containing alkylene carbonic acid ester units as well. However, the carbon atoms of the alkylene groups art not oxysubstituted and have thus no adjacent hydroxyl nor hydrolysable ester, ortho ester or acetal residues. They are thus less biodegradable. The polyesters are used for medical devices, e.g. implants, to aid in tissue regeneration, growth and/or healing and act as medical devices not contain drug compounds.

In the German Patent Application 1,921,866 polyesters are described, prepared by reacting a) diphenyl carbonate, b) a diol, like neopentyl glycol and c) a triol, e.g. hexanetriol-1,2,6 (Example 40) or a tetrol. They were said to have an undefined structure. The polyesters are used for the preparation of weatherproof and ultra-violet light resistant protective coatings. The structure of the compounds of the invention is well defined and different, since those having $(C_{4-10})$alkylene groups possess at least 2 oxy substituents compared with 1 oxy substitutent in the $C_6$-alkylene unit of Example 40.

The preparation of the pharmaceutical forms according to the invention may be carried out by methods known per se, the microparticles and microcapsules by appropriate spray drying or emulsifying techniques, the implants by mixing the drug compound and the polyesters both in particulated, solid state at higher temperatures at which the polyesters become liquid, followed by cooling the mixture to solid state and modelling it to a suitable shape. It is also possible to mix the drug compound in dissolved or dispersed state with a solution of the polyester and to evaporate the solvent, after which the solid residue is shaped to suitable implant forms.

Pharmaceutical compositions containing microparticles may be made by working them up with suitable galenical excipients and optionally bringing them in appropriate dispensers.

Whereas in implants the drug loading content can vary between wide limits, in the order of 0.001 to about 70%, the loading content of microparticles and microcapsules can— due to the method of their production—vary between narrower limits, e.g. 0.001 to 8% of weight.

The choice of pharmacologically active compound to be used in combination with the polyesters of the invention is not critical. In the case of microparticles or microcapsules preferably those types of drug compounds are used, which are pharmacologically active in low amounts and need to have an uninterrupted blood level during extended periods, e.g. peptides or proteins, e.g. somatostatins or interleukins, but especially such of hormonal types, in particular those that will desintegrate after oral use in the gastro-intestinal system and thus preferably are administered parenterally.

The depot formulation according to the invention may be used to administer a wide variety of classes of active agents, e.g. pharmacologically active agents such as contraceptives, sedatives, steroids, sulphonamides, vaccines, vitamins, anti-migraine drugs, enzymes, bronchodilators, cardiovascular drugs, analgesics, antibiotics, antigens, anti-convulsive drugs, anti-inflammatory drugs, anti-parkinson drugs, prolaction secretion inhibitors, anti-asthmatic drugs, geriatrics and anti-malarial drugs.

The depot formulations may be used for the known indication of the particular drug compound incorporated therein.

The exact amounts of drug compound and of the depot formulation to be administered depends on a number of factors, e.g. the condition to be treated, the desired duration of treatment, the rate of release of drug compound and the degradability of the polyester matrix.

The desired formulations may be produced in known manner. The amount of the pharmacologically active agent required and the release rate thereof may be determined on the basis of known in vitro or in vivo techniques, e.g. how long a particular active agent concentration in the blood plasma remains at an acceptable level. The degradability of the matrix may also be obtained by in vitro or especially in vivo techniques, for example wherein the amount of matrix materials in the muscle is weighed after particular time periods, e.g. in comparison with other matrix materials.

The depot formulations of the invention may be administered in the form of e.g. microparticles, e.g. orally or preferably subcutaneously or intramusculary, particularly as a suspension in a suitable liquid carrier or in the form of implants, e.g. sub-cutaneously.

Repeated administration of the depot formulations of the invention may be effected when the polyester matrix has sufficiently been degraded, e.g. after 1, 2 or 3 weeks or 1 month.

An example of a dose is as follows:
20 mg of octreotide in a polymer as described in Example 37 to be administered s.c. once a month against acromegaly.

An advantage of the polyester matrices of the invention is that during and after the release of the drug compound many of them may be quickly degraded to a molecular size, which may be transported by the body fluids from the site of administration.

EXPERIMENTAL

General

Materials

Figure 1:
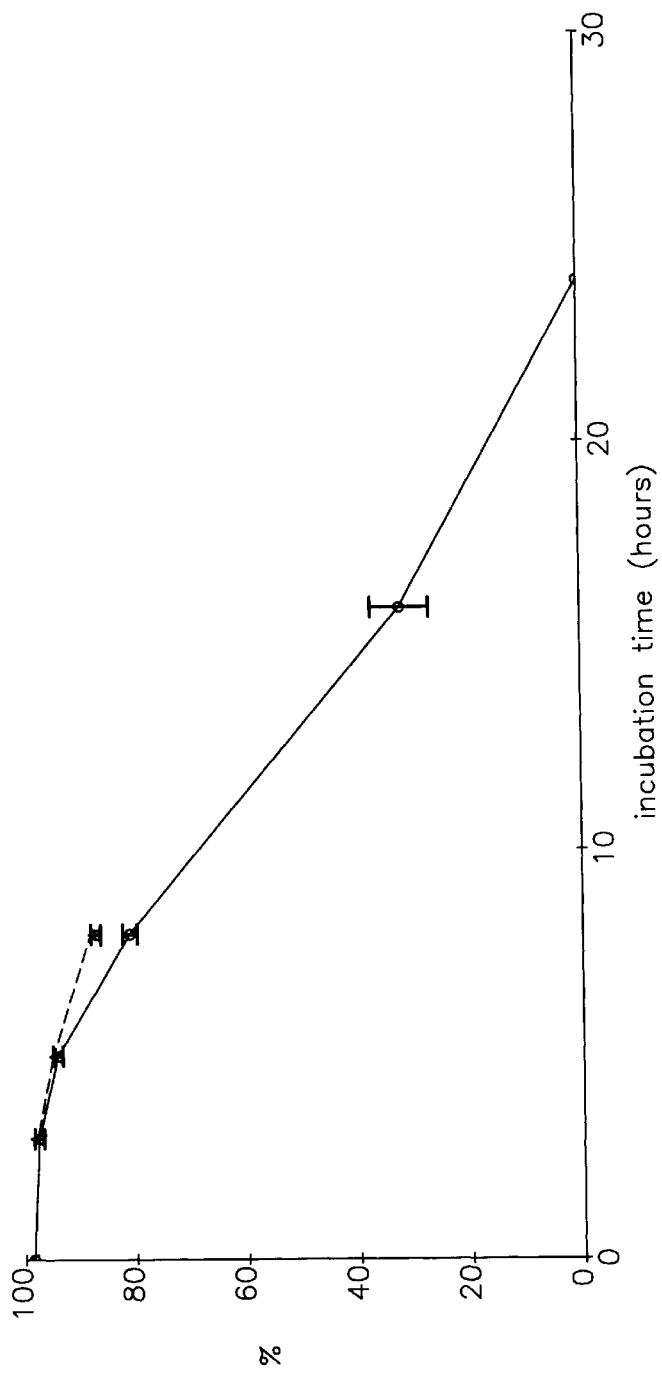
FIG. 1 is a graph of polymer (monomer units 9C) in vitro degradation.

To each prepared polyester a number was given. On the formula page the corresponding alkylene carbonic acid ester unit has been designed, related to this number. Letter (a), (b), or (c) as a suffix to the compound number denotes that the polymer was derived from L-, D-, or DL-sugar alcohols.

2,4:3,5- and 2,3:4,5-di-O-isopropylidene-D-mannitol were prepared by a modified version of the procedure described in:

[27] K. Gavronska, Carbohydr. Res. 176, 79, (1988).

The starting material was 1,5-di-O-benzoyl-D-mannitol:

[28] P. Brigl and H. Grüner, Berchte 65 641 (1932).

Hyflo (Super) Cel (Kieselgur, 2–25 microns, Fluka 56678) was used as filtration aid.

Molecular weights (Mw=weight average molecular weight; Mn=number average molecular weight) were determined by gel permeation chromatography on a Waters 840 system with a refraction index detector Waters 410 and UV detector Waters 490. Columns: polystyrene-divinylbenzene crosslinked gels, Polymer Laboratories, UK, combination of columns with pores of $10^5$, $10^4$ and 500 Angstroms, at 35° C. Calibration with standard polystyrenes, Polymer Laboratories, UK, for a molecular weight range of $1.75 \times 10^6$ to 580 Daltons.

Glass transition temperatures (Tg) and melting points (Tm) were measured on a DSC 7 instrument of Perkin Elmer with data station and intracooler at a scanning rate of 10°

C./min. heating. The sample was heated in a first run above the glass transition temperature followed by fast cooling to −30° C. and a second run to give the Tg-value.

Inherent viscosities (=$\eta_{inh}$) were measured at 20° C. on an AVS 350 instrument with a Micro-Ubbelohde capillary.

NMR spectra were obtained on a Bruker AM 360 spectrometer. (δ) in NMR-data means the chemical shift delta, given in ppm. The assignments of the NMR-signals to the nuclei are not proved. Therefore, some of the assignments may be interchangeable.

The empirical formulae in the microanalysis results are those of the corresponding monomer units of the polyesters.

Formula pages are to be found at the end of the examples.

EXAMPLE 1

The Polyester from (+)-2,3-O-Isopropylidene-L-Threitol and Diethyl Carbonate
(Monomer Unit 1a, See Formula Pages)

39.7 g (245 mol) of (+)-2,3-O-isopropylidene-L-threitol (see formula pages) were placed in a dry, round bottomed flask, which is a part of a distillation apparatus. 190 ml (1570 mmol) of diethyl carbonate and 0.794 g of di-n-butyl-tin-oxide were added while in an atmosphere of argon. The reaction mixture was stirred at 120° C. for 20 hrs., during which time distillation occurred. After cooling to room temperature, the distillate was removed under argon and then the pressure was carefully reduced to 45 mbars. The mixture was heated to 65° C. and stirred at this temperature for 4.5 hrs. to distill the excess diethyl carbonate. After the distillation was completed, the pressure was set to atmospheric pressure with argon and the distillate was removed while under argon. Then the pressure was reduced to 8 mbars and the temperature was increased stepwise to 120° C. during 1 hr. The reaction mixture was stirred for 48 hrs. at 120° C./8 mbars and for 20 hrs. at 130° C./0.3 mbar. For working-up, the reaction mixture was cooled to room temperature, dissolved in 150 ml of dichloromethane under reflux and 3 g of Hyflo Cel were added to the solution. After stirring for 15 min. at room temperature, the suspension was filtered and the polymeric product was precipitated by slow addition of the dichloromethane solution into 2000 ml of methanol. The brownish-beige precipitate was dissolved in 600 ml of acetone and treated slowly while continuously stirring, with 1 ml of a 30% solution of hydrogen peroxide in water. The mixture was stirred at room temperature for 20 hours. Then, the solution was treated with 4 g of a filtering aid (Hyflo Cel), stirred for another 1 hr. and filtered. The solvent was evaporated under reduced pressure, the residue dissolved in 70 ml of dichloromethane and the product precipitated by dropwise addition of the dichloromethane solution to 2000 ml of methanol. The precipitate was dried in vacuo for 48 hrs. to give the polyester in almost colourless, white solid form.

$\eta_{inh}$(dl/g)=0.115 in CHCl$_3$ Mw=11350 Da, Mn=8250 Da, Mw/Mn=1.38 Tg=51.3° C. [alpha]$_D$=−34° (c=1 in CHCl$_3$, 20° C.) IR (KBr): 2992 m, 2942 w, 2908 w, 1757 s, broad, 1460 m, 1386 s, 1235 s, broad, 1169 m, 1092 s, 992 m, 964 m, 845 m, 786 m, 607 w, 514 m [cm$^{-1}$]. $^1$H-NMR (CDCl$_3$, 360 MHz): δ=1.42 ppm (s, 6H, 2CH$_3$); 4.096 (m, 2H, 2CH); 4.245 (d.m, $^2$J$_{AB}$=ca. 11.5 Hz, 2H, 2H$_B$ of 2CH$_2$); 4.357 (d.d, $^2$J$_{AB}$=ca. 11.5 Hz and J=ca. 3.3 Hz, 2H, 2H$_A$ of 2CH$_2$). $^{13}$C-NMR (CDCl$_3$, 90 MHz): δ=154.59 ppm (O—C(O)—O); 110.55 (O—C—O); 75.34 (CH); 67.17 (CH$_2$); 26.83 (CH$_3$). Microanalysis: Calc. for C$_8$H$_{12}$O$_5$: C 51.08%, H 6.38% found: 50.90%, 6.50%

EXAMPLE 2

The Polyester from (−)-2,3-O-Isopropylidene-D-Threitol and Diethyl Carbonate
(Monomer Unit 1b)

Polycondensation of 40.0 g (247 mmol) of (−)-2,3-O-isopropylidene-D-threitol with diethyl carbonate according to the procedure described in example 1) gave the polyester having the monomer unit 1b.

$\eta_{inh}$(dl/g)=0.145 in CHCl$_3$ Mw=14700 Da, Mn=9950 Da, Mw/Mn=1.48 Tg=52.2° C. [alpha]$_D$=+33.5° (c=1 in CHCl$_3$, 20° C.) IR- and NMR-Spectra of the polymer of 1b were identical with the spectra of the polymer of 1a. Microanalysis: Calculated for C$_8$H$_{12}$O$_5$: C 51.08%, H 6.38% found: 50.80%, 6.50%

EXAMPLE 3

The Polyester from 2,3-O-Isopropylidene-DL-Threitol and Diethyl Carbonate (Monomer Unit 1c)

39.53 g (244 mmol) of (+)-2,3-O-isopropylidene-L-threitol and 39.53 g (−)-2,3-O-isopropylidene-D-threitol were placed in a dry, round bottomed flask, as a part of a distillation apparatus. 370 ml (3050 mmol) of diethyl carbonate and 1.6 g of di-n-butyl-tin-oxide were added in an atmosphere of argon. The mixture was stirred for 16 hrs. at room temperature and for additional 20 hrs. at 120° C., during which period distillation occurred. After cooling to room temperature, the distillate was removed under argon and the pressure was carefully reduced to 50 mbars. The temperature was increased stepwise to 100° C. during 3 hrs. to distill the excess diethyl carbonate. After the distillation was completed, the pressure was set to atmospheric pressure with argon and the distillate was removed in an argon atmosphere. Then, the pressure was reduced to 8 mbars and the temperature was increased stepwise to 120° C. during 1 hr. The reaction mixture was stirred for 20 hrs. at 120° C./8 mbars and for 20 hrs. at 140° C./0.5 mbars.

For working-up, the product mixture was cooled to 40° C. and dissolved in 600 ml of dichloromethane under reflux. The solution was treated with 6 g Hyflo Cel, stirred for 1 hr. at room temperature and filtered. The solvent was evaporated to a final volume of ca. 250 ml under reduced pressure and the polymeric product was precipitated by dropwise addition of the solution to 4000 ml of methanol. The brownish-beige precipitate was dissolved in 1500 ml of acetone and 2.2 ml of 30% hydrogen peroxide in water were added slowly to the stirred solution. The mixture was stirred at room temperature for 20 hours. The solution was then treated with 6 g of Hyflo Cel, stirred for another 1 hr. and filtered. The solvent was evaporated at reduced pressure, the residue dissolved in ca. 250 ml of dichloromethane and the product was precipitated by dropwise addition of the dichloromethane solution to 4000 ml of methanol. Drying of the precipitate in vacuo for 48 hrs. gave the polyester as an almost colourless white solid.

The mother liquor was evaporated, the residue dissolved in 20 ml of dichloromethane and precipitated from 1000 ml of methanol to give, after drying in vacuo, an additional amount of polyester.

$\eta_{inh}$(dl/g)=0.145 in CHCl$_3$ Mw=16550 Da, Mn=10300 Da, Mw/Mn=1.61 Tg=47.50° C. IR (KBr): 2990 m, 2940 m, 2907 m, 1757 s, broad, 1576 w, 1457 m, 1385 s, 1233 s, broad, 1169 m, 1092 s, 993 m, 963 m, 845 m, 786 m, 737 w, 607 w, 513 m [cm$^{-1}$].

$^1$H-NMR (CDCl$_3$, 360 MHz): δ=1.42 ppm (s, 6H, 2CH$_3$); 4.10 (m, 2H, 2CH); 4.24 (d.m, $^2$J$_{AB}$=ca. 11.5 Hz, 2H, 2H$_B$ of 2CH$_2$); 4.357 (d.d, $^2$J$_{AB}$=ca. 11.5 Hz and J=ca. 3.3 Hz, 2H, 2H$_A$ of 2CH$_2$).

$^{13}$C-NMR (CDCl$_3$, 90 MHz): δ=154.61 ppm (O—C(O)—O); 110.57 (O—C—O); 75.34 (CH); 67.20 (CH$_2$); 26.86 (CH$_3$). Microanalysis: Calculated for C$_8$H$_{12}$O$_5$: C 51.08%, H 6.38% found: 50.60%, 6.30%

Additional polyesters of different molecular weights having the monomer unit 1c were prepared by varying reaction conditions such as temperature, pressure and reaction time, see next table.

| Temp. [°C.] | Mw [Da] | Mn [Da] | Mw/Mn | Tg [°C.] |
|---|---|---|---|---|
| 120.0* | 10700 | 6450 | 1.66 | 42.0 |
| 140.0* | 20300 | 11100 | 1.83 | 47.0 |
| 150.0* | 23400 | 12700 | 1.84 | 50.1 |
| ** | 42000 | 27200 | 1.54 | 54.5 |

*24 h, 120° C./1013 mbar, then 3 × 24 h at given temperature and 400 mbar, 100 mbar and 0.2 mbar respectively (total reaction time 96 hours for each compound)
**24 h/120° C./1013 mbar, 24 h/120° C./8 mbar, 30 h/140° C./0,35 mbar, 30 h/160° C./0.35 mbar

EXAMPLE 4
Synthesis of the Polyester Having the Monomer Unit 2a

To a stirred solution of 18.82 g (100 mmol) of the polyester having the monomer unit 1a (of Example 1) in 150 ml of dichloromethane were added 27 ml of water and 150 ml of trifluoroacetic acid. The reaction mixture was stirred rigorously for 20 minutes at room temperature. The product was then precipitated by dropwise addition of the solution to 3000 ml of diethyl ether. The suspension was stirred for additional 10 minutes at room temperature, the precipitate was isolated under an argon stream and washed twice with diethyl ether. Drying in vacuo for 48 hours gave the polyester as a hygroscopic, white powder, which was kept under argon.

The polyester is soluble in water, dimethylformamide and dimethyl sulphoxide. It is insoluble or hardly soluble in chloroform, dichloromethane, tetrahydrofuran, dioxane, ethyl acetate and acetone. In some solvents its dissolution may be accompanied by degradation.

$\eta_{inh}$(dl/g)=0.085 in $H_2O$ Tg=31.4° C.

IR (KBr): 3447 s, broad, 2967 w, 2917 w, 1750 s, broad, 1460 m, 1408 m, 1282 and 1262 s, broad, 1134 m, 1077 m, 960 m, 895 w, 788 m [$cm^{-1}$].

$^1$H-NMR ($d_6$-DMSO, 360 MHz): δ=3.697 ppm (m, 2H, 2CH); 4.044 (d.d, $^2J_{AB}$=ca. 10.7 Hz and J=ca. 7 Hz, 2H, $2H_B$ of $2CH_2$); 4.125 (d.d, $^2J_{AB}$=ca. 10.7 Hz and J=ca. 4 Hz, 2H, $2H_A$ of $2CH_2$); ca. 4.76 (broad s, 2H, 2OH).

$^{13}$C-NMR ($d_6$-DMSO, 90 MHz): δ=154.59 ppm (O—C(O)—O); 68.62 ($CH_2$); 68.37 (CH).

Microanalysis: Calculated for $C_5H_8O_5$: C 40.56%, H 5.40% found: 39.90%, 5.60%

EXAMPLE 5
Synthesis of the Polyester Having the Monomer Unit 2b 14.11 g (75 mmol) of the polyester having the monomer unit 1b (of Example 2) were hydrolysed with trifluoroacetic acid (112.3 ml) and water (20.2 ml) in dichloromethane (112 ml) according to the procedure described in Example 4) to give the polyester having the monomer unit 2b. The polymer has similar dissolution properties as the polymer of 2a.

$\eta_{inh}$(dl/g)=0.07 in $H_2O$ Tg=32.3° C.

IR- and NMR-Spectra of the polymer of 2b were identical to those of the polymer of 2a.

Microanalysis: Calculated for $C_5H_8O_5$: C 40.56%, H 5.40% found: 39.20%, 5.50%

EXAMPLE 6
Synthesis of the Polyester Having the Monomer Unit 2c 58.68 g (312 mmol) of the polyester having the monomer unit 1c (of Example 3) were hydrolysed with 470 ml of trifluoroacetic acid and 85 ml of water in 470 ml dichloromethane according to the procedure described in Example 4), leading to the formation of the polyester.

$\eta_{inh}$(dl/g)=0.1 in $H_2O$
Tg=39.6° C.

IR (KBr): 3468 s, broad, 2968 w, 2917 w, 1751 s, broad, 1458 m, 1409 m, 1284 and 1259 s, broad 1132 m, 1075 m, 959 m, 895 w, 787 m [$cm^{-1}$].

$^1$H-NMR ($d_6$-DMSO, 360 MHz): δ=3.696 ppm (m, 2H, 2CH); 4.044 (d.d, $^2J_{AB}$=ca. 10.7 Hz and J=ca. 7 Hz, 2H, $2H_B$ of $2CH_2$); 4.125 (d.d, $^2J_{AB}$=ca. 10.7 Hz and J=ca. 4 Hz, 2H, $2H_A$ of $2CH_2$); ca. 4.91 (broad s, 2H, 2 OH).

$^{13}$C-NMR ($d_6$-DMSO, 90 MHz): δ=154.55 ppm (O—C(O)—O); 68.58 ($CH_2$); 68.32 (CH). Microanalysis: Calculated for $C_5H_8O_5$: C 40.56%, H 5.40% found: 40.90%, 5.60%

EXAMPLE 7
Synthesis of the Polyester Having the Monomer Unit 3a 2 g (13.5 mmol) of the polyester having the monomer unit 2a (of Example 4) was suspended in 30 ml of dry tetrahydrofuran. 0.55 ml pyridine and 32 ml acetic anhydride were added to the suspension in an argon atmosphere. The mixture was stirred for 18 hrs. at room temperature, then the solvent was evaporated under reduced pressure and the residue was dissolved in 10 ml of dichloromethane. The product was precipitated by dropwise addition of the solution to 250 ml of tert.-butyl methyl ether. The precipitate was washed with 100 ml of water, resolved in 10 ml of dichloromethane and reprecipitated from 250 ml of tert.-butyl methyl ether. Drying of the precipitate in vacuo for 120 hrs. at 50° C. gave the polyester as a fine, white powder.

$\eta_{inh}$(dl/g)=0.11 in $CHCl_3$
Mw=10950 Da, Mn=7750 Da, Mw/Mn=1.41
Tg=56.2° C.

IR (KBr): 2978 w, 1751 s, broad, 1456 w, 1410 w, 1376 m, 1279 shoulder, 1217 s, broad, 1057 m, 1015 w, 951 w, 847 w, 787 m, 632 w, 603 w [$cm^{-1}$].

$^1$H-NMR ($CDCl_3$, 360 MHz): δ=2.12 ppm (s, 6H, $2CH_3$); 4.165 (d.d, $^2J_{AB}$=ca. 11.8 Hz and J=ca. 5.6 Hz, 2H, $2H_B$ of $2CH_2$); 4.385 (d.d, $_2J_{AB}$=ca. 11.8 Hz and J=ca. 3.3 Hz, 2H, $2H_A$ of $2CH_2$); 5.339 (m, 2H, 2CH).

$^{13}$C-NMR ($CDCl_3$, 90 MHz): δ=169.82 ppm (—C(O)—O); 154.22 (O—C(O)—O); 68.68 (CH); 65.67 ($CH_2$); 20.66 ($CH_3$).

Microanalysis: Calculated for $C_9H_{12}O_7$: C 46.57%, H 5.17% found: 46.30%, 5.40%

EXAMPLE 8
Synthesis of the Polyester Having the Monomer Unit 3b 2 g (13.5 mmol) of the polyester having the monomer unit 2b (of Example 5) were acetylated according to the procedure described in example 7) to give the polyester as a fine, white powder.

$\eta_{inh}$(dl/g)=0.10 in $CHCl_3$
Mw=11250 Da, Mn=7300 Da, Mw/Mn=1.54
Tg=58.6° C.

IR- and NMR-Spectra of the polymer of 3b were identical to those of the polymer of 3a.

Microanalysis: Calculated for $C_9H_{12}O_7$: C 46.57%, H 5.17% found: 45.20%, 5.20%

EXAMPLE 9
Synthesis of the Polyester Having the Monomer Unit 3c 6.07 g (41 mmol) of the polyester having the monomer unit 2c (of Example 6) were acetylated with 97 ml of acetic anhydride and 1.7 ml of pyridine in 90 ml of tetrahydrofuran according to the procedure described in Example 7) to give the polyester as a fine, white powder.

$\eta_{inh}$(dl/g)=0.14 in CHCl$_3$
Mw=13800 Da, Mn=9050 Da, Mw/Mn=1.52
Tg=57.8° C.
IR (KBr): 2977 w, 1750 s, broad, 1449 w, 1411 w, 1376 m, 1279 shoulder, 1216 s, broad, 1057 m, 1015 w, 951 w, 847 w, 787 m, 631 w, 603 w [cm$^{-1}$].
$^1$H-NMR (CDCl$_3$, 360 MHz): δ=2.12 ppm (s, 6H, 2CH$_3$); 4.17 (m, 2H 2H$_B$ of 2CH$_2$); 4.38 (d.m, $^2J_{AB}$=ca. 12.1 Hz, 2H, 2H$_A$ of 2CH$_2$); 5.328 (m, 2H, 2CH).
$^{13}$C-NMR (CDCl$_3$, 90 MHz): δ=169.79 ppm (—C(O)—O); 154.21 (O—C(O)—O); 68.70 (CH); 65.66 (CH$_2$); 20.66 (CH$_3$).
Microanalysis: Calculated for C$_9$H$_{12}$O$_7$: C 46.57%, H 5.17% found: 46.70%, H 5.40%

EXAMPLE 10
Synthesis of the Polyester Having the Monomer Unit 4c 86.31 g (1.875 mol) of formic acid were added dropwise into 127.6 g (1.25 mol) of acetic anhydride. The temperature was kept below 40° C. during this exothermic step. After the addition was completed, the mixture was stirred for 1 hr. at 50° C., then cooled to room temperature and 7.4 g (50 mmol) of the polyester of Example 6 (monomer unit 2c) were added. The suspension was cooled in an ice bath and 59.3 g (0.75 mol) of pyridine were added dropwise to the suspension at 0° C. When the addition of pyridine was completed, the suspension was stirred for 1.5 hrs. at 0° C. and for additional 18 hrs. at room temperature then filtered and the product was precipitated by dropwise addition of the filtrate to 1500 ml of diethyl ether. The precipitate was redissolved in 15 ml of acetone and reprecipitated by dropwise addition of the solution into 1500 ml of diethyl ether. The precipitate was filtered and dried in vacuo at room temperature to yield a polyester having the monomer unit 4c as a fine, white powder.

$\eta_{inh}$(dl/g)=0.065 in acetone
Tg=54.3° C.
IR (KBr): Strong absorptions at 1758, 1727, 1251 and 1154 cm$^{-1}$.
$^1$H-NMR (d$_6$-DMSO, 360 MHz): δ=4.275 ppm (dd, $^2J_{AB}$=ca. 12 Hz and J=ca. 6 Hz, 2H, 2H$_B$ of 2CH$_2$); 4.34 (d, $^2J_{AB}$=ca. 12 Hz, 2H, 2H$_A$ of 2 CH$_2$); 5.40 (m, 2H, 2CH); 8.30 (s, 2H, 2H—C(O)—O).
$^{13}$C-NMR (d$_6$-DMSO, 90 MHz): δ=65.58 ppm (CH$_2$); 68.11 (CH); 153.54 (O—C(O)—O); 161.06 (H—C(O)—O).
Microanalysis: Calculated for C$_7$H$_8$O$_7$: C 41.20%, H 3.92% found: 41.30%, 4.00%

EXAMPLE 11
Synthesis of the Polyester Having the Monomer Unit 5a 1.85 g (12.5 mmol) of the polyester of Example 4 (monomer unit 2a) were dissolved in 8 ml dimethylformamide and the solution was diluted with 30 ml of tetrahydrofuran. 0.495 g (6.25 mmol) pyridine and 38.8 g (181 mmol) caproic anhydride were added under argon and the mixture was stirred for 20 hrs. at room temperature. The solution was then diluted with 50 ml of dichloromethane, washed twice with saturated sodium bicarbonate solution and with water, the organic layer was separated and dried over anhydrous sodium sulfate. The solvent was evaporated under reduced pressure, the residue was dissolved in 15 ml of dichloromethane and the polymeric product was precipitated by dropwise addition of this solution to 600 ml of hexane. Reprecipitation from dichloromethane/hexane and drying in vacuo for 48 hrs. gave a polyester having the monomer unit 5a as a viscous oil. According to $^1$H-NMR, 76% of the hydroxyl groups were esterified to caproate ester and 24% were present in free condition. Thus, the product comprised approximately 52% di-caproate ester units (di-units) and 48% mono-caproate ester units (mono-units). The ratio of di-units and mono-units was determined from the integrals of the signals at 5.352 ppm (2CH of di-units) and 5.205 ppm (1CH of mono-units).

$\eta_{inh}$(dl/g)=0.08 in CHCl$_3$
Mw=7550 Da, Mn=5000 Da, Mw/Mn=1.51
Tg=9.9° C.
IR (film): Strong absorptions at 1750, 1246 and 1164 cm$^{-1}$.
$^1$H-NMR (CDCl$_3$, 360 MHz): δ=0.899 ppm (t, J=7 Hz, CH$_3$ of caproate side chain); 1.317 (m, 2CH$_2$ of caproate side chain); 1.55–1.70 (m, CH$_2$ of caproate side chain); 2.26–2.44 (m, CH$_2$ of caproate side chain); 4.02–4.56 (m, 2CH$_2$ of di-units, 2CH$_2$ of mono-units, 1CH of mono-units and OH of mono-units); 5.205 (m, 1CH of mono-units); 5.352 (m, 2CH of di-units).
$^{13}$C-NMR (CDCl$_3$, 90 MHz): δ=172.9 and 172.6 ppm (—C(O)—O); ca. 154.5 (multiple signal, O—C(O)—O); ca. 70.1 (multiple signal, CH); ca. 68.6 (multiple signal, CH); ca. 65.8 (multiple signal, CH$_2$); 33.97 (CH$_2$ of caproate side chain); 31.17 (CH$_2$ of caproate side chain); 24.46 (CH$_2$ of caproate side chain); 22.26 (CH$_2$ of caproate side chain); 13.87 (CH$_3$).

EXAMPLE 12
Synthesis of the Polyester Having the Monomer Unit 6a 1.48 g (10 mmol) of the polymer having the monomer unit 2a (of Example 4) and 1.7 ml pyridine were dissolved in 60 ml of dimethylformamide/tetrahydrofurane (1:1). A solution of 12.12 g (40 mmol) of stearoyl chloride in 30 ml of tetrahydrofuran was added dropwise over 15 minutes to the stirred solution at room temperature and stirring was continued for additional 20 hours. The solvent was then evaporated under reduced pressure, the residue dissolved in 200 ml of dichloromethane and washed with aequous 5% sodium bicarbonate (2×) and water. The organic layer was dried over anhydrous sodium sulfate, the solution concentrated to a final volume of 100 ml and the product was precipitated by dropwise addition of the solution to 2000 ml of methanol. The precipitate was dissolved in 350 ml of ethyl acetate at 60° C. and the stirred solution was allowed to cool to room temperature. After 2 hours stirring at room temperature, the white, powdery precipitate was isolated and dried in vacuo for 48 hours at room temperature to give the polyester. The reprecipitation from ethyl acetate was repeated to give the product with a low polydispersity. According to $^1$H-NMR, ca. 95% of the hydroxyl groups were stearoylated and ca. 5% were in free condition. Thus, the product comprised ca. 90% of di-stearoylated units (=di-units) and ca. 10% of mono-stearoylated units (=mono-units). The ratio of di-stearoylation and mono-stearoylation was determined from the integrals of the signals at ca. 5.34 ppm (2CH of di-units) and ca. 5.20 ppm (1CH of mono-units). Other signals of the minor mono-units were either overlapping with the signals of the major di-units or were too small to observe. Thus, the $^1$H-NMR spectrum of the product is mainly attributed to the major di-units.

$\eta_{inh}$(dl/g)=0.11 in CHCl$_3$
Mw=15850 Da, Mn=13500 Da, Mw/Mn=1.17
Tm=55° to 75° C.
IR (KBr): Strong absorptions at 2918, 2850, 1751 and 1250 cm$^{-1}$.
$^1$H-NMR (CDCl$_3$, 360 MHz): δ=0.88 ppm (t, J=ca. 6.8 Hz, various CH$_3$); 1.20–1.35 (m, various CH$_2$); 1.605 (m, various CH$_2$); 2.33 (m, various CH$_2$); 4.05–4.25 (m, 2H$_B$ of 2CH$_2$—O of di-units and various H of mono-units); 4.375 (d.m, $^2J_{AB}$=ca. 11 Hz, 2H$_A$ of 2CH$_2$—O of di-units and various H of mono-units); ca. 5.20 (m, 1CH of mono-units); 5.34 (m, 2CH of di-units).

EXAMPLE 13
Synthesis of the Polyester Having the Monomer Unit 7c 2.96 g (20 mmole) of the polyester having the monomer unit 2c (of Example 6) were dissolved in 90 ml dimethylformamide/tetrahydrofuran (1:5) and the solution was cooled to 0° C. in an ice bath. 3.56 g (45 mmole) pyridine and a solution of 9.23 g (50 mmole) Benzyloxyacetyl chloride in 60 ml of tetrahydrofuran were added subsequently to the stirred solution at 0° C. and stirring was continued for additional 6 hours at this temperature. Then, the mixture was dissolved in 300 ml of dichloromethane, the dichloromethane solution was washed with aqeuous 5% sodium bicarbonate (2×) and water (2×) and dried over anhydrous sodium sulfate. The solvent was then evaporated under reduced pressure and the residue was dissolved in 30 ml of dichloromethane. The polyester was precipitated on dropwise addition of this solution into 1000 ml of methanol and dried for 48 hours in vacuo.

$\eta_{inh}$(dl/g)=0.12 in $CHCl_3$
Mw=17550 Da, Mn=11200 Da, Mw/Mn=1.57
Tg=32.2° C.
IR (film): Strong absorptions at 1762, 1246, 1185 and 1125 $cm^{-1}$.
$^1$H-NMR ($CDCl_3$, 360 MHz). δ=4.00–4.19 ppm (m, 6H, $2H_B$ of 2 chain $CH_2$ and $2CH_2$); ca. 4.35 (m, 2H, $2H_A$ of 2 chain $CH_2$); 4.555 (m, 4H, 2 benzyl $CH_2$); 5.383 (m, 2H, 2CH); 7.20–7.40 (m, 10H, arom.H).
$^{13}$C-NMR ($CDCl_3$, 90 MHz): δ=169.41 ppm (—C(O)—O); 154.06 (O—C(O)—O); 136.87 (arom.C); 128.41 and 127.94 (arom. CH); 73.27 (benzyl $CH_2$); 69.00 (CH); 66.73 ($CH_2$); 65.54 (chain $CH_2$).
Microanalysis: Calc. for $C_{23}H_{24}O_9$: C 62.18%, H 5.40% found: 61.50%, 5.60%

EXAMPLE 14
Synthesis of the Polyester Having the Monomer Unit 8c 1 g of 5% palladium on charcoal was suspended in 250 ml of dioxane and dimethylformamide (9:1) while under argon. Hydrogen gas was bubbled through the suspension during 30 minutes. To the stirred suspension was added dropwise, while the bubbling of the hydrogen gas was continued, a solution of 5 g (11.25 mmol) of the polyester having the monomer unit 7c (Mw=12200, Mn=8300) in 250 ml of dioxane/dimethylformamide (9:1). The mixture was stirred for additional 2 hours under a gentle stream of hydrogen, then purged with argon. The catalyst was removed by filtration. The filtrate was evaporated in vacuo to a final volume of ca. 75 ml. and by addition of this solution into 500 ml of isopropyl ether a product was precipitated. The precipitate was dissolved in 50 ml of dioxane and stirred with 150 mg of activated charcoal at room temperature. After filtration, the filtrate was evaporated in vacuo to a final volume of ca. 15 ml and a product was precipitated by dropwise addition of this solution to 500 ml of isopropyl ether. The product was dried in vacuo for 48 hours to yield the polyester having the monomer unit 8c.

$\eta_{inh}$. (dl/g)=0.105 in $CHCl_3$
Tg=44,8° C.
IR (KBr): Strong absorptions at 3446, 1757, 1255, 1193 and 1094 $cm^{-1}$.
$^1$H-NMR ($d_6$-DMSO, 360 MHz): δ=4.05 ppm (m, 4H, 2 side chain $CH_2$); 4.15–4.24 (m, 2H, $2H_B$ of $CH_2$); ca. 4.29 (d.m, J=ca. 11 Hz, 2H, $2H_A$ of 2 $CH_2$); ca. 5.35 (m, 2H, 2CH); 5.42 (t, J=6.5 Hz, 2H, 2OH).
$^{13}$C-NMR ($d_6$-DMSO, 90 MHz): δ=172.00 ppm (—C(O)—O); 153.72 (O—C(O)—O); 68.62 (CH); 65.68 ($CH_2$); 59.33 (side chain $CH_2$).

Microanalysis: Calculated for $C_9H_{12}O_9$: C 40.92% H 4.58% found: 40.85% 4.85%

Additional esterifications with active lactic- or glycolic acid derivatives lead to products having oligo- and poly-co-glycolide-lactide side chains.

Polyesters having monomer units 2a–2c are alternatively derivatized with glycolic- or lactic acid ester residues by treatment with the corresponding chloroformates, utilizing the hydroxyl groups of glycolic respectively lactic acid residues. The conversion of e.g. ethyl lactate into ethyllactyl chloroformate is described in the literature [29]: U.S. Pat. No. 3,742,022 (1973) and [30]: German Patent 26 58 254 (1977). Treatment of the polyester having the monomer unit 2c with ethyllactyl chloroformate according to the procedure described in examples 21 or 22 gives the corresponding ethyllactyl carbonate derivative.

EXAMPLE 15
Synthesis of the Polyester Having the Monomer Unit 9c 2.22 g (15 mmol) of the polyester of Example 6 (monomer unit 2c) were dissolved in 12 ml dimethylformamide, the solution was diluted with 60 ml of tetrahydrofuran and 3.34 g (33 mmol) of 4-methylmorpholine were added. The solution was cooled down to 0° C. in an ice-bath and treated dropwise with a solution of 3.17 g (30 mmol) pyruvoyl chloride in 17 ml of tetrahydrofuran. The mixture was stirred for 4 hrs. at 0° C., the solvent was removed under reduced pressure and the residue was taken up in 400 ml of dichloromethane. The solution was washed twice with water, dried over anhydrous sodium sulfate, filtered and the solvent was evaporated under reduced pressure. The residue was dissolved in 15 ml of dichloromethane and the product was precipitated by dropwise addition of the solution into 500 ml of diethyl ether. The product was reprecipitated from dichloromethane/diethyl ether and dried in vacuo for 48 hrs. to give a polyester having the monomer unit 9c as a brownish-yellow powder.

$\eta_{inh}$(dl/g)=0.05 in $CHCl_3$
Mw=5950, Mn=3750, Mw/Mn=1.59
Tg=50.3° C.
IR (KBr): Strong absorptions at 1768, 1739, 1251 and 1135 $cm^{-1}$.
$^1$H-NMR ($CDCl_3$, 360 MHz): δ=2.47 ppm (m, 6H, $2CH_3$); 4.33 (m, 2H, $2H_B$ of $2CH_2$); 4.51 (m, 2H, $2H_A$ of $2CH_2$); 5.47 (m, 2H, 2CH).
$^{13}$C-NMR ($CDCl_3$, 90 MHz): δ=ca. 190.3 ppm (—C(O)—); 159.41 (—C(O)—O); 153.99 (O—C(O)—O); 70.60 (CH); 65.15 ($CH_2$); 26.69 ($CH_3$).
Microanalysis: Calculated for $C_{11}H_{12}O_9$: C 45.84%, H 4.20% found: 45.40%, 4.20%

EXAMPLE 16
Synthesis of the Polyester Having the Monomer Unit 10c 9.12 g (60.8 mmol) of benzoyl formic acid were treated slowly with 6.99 g (60.8 mmol) of dichloromethyl methyl ether and the mixture was stirred at 50° C. (bath temp.) for 90 minutes, until HCl-evolution was almost ceased. The mixture was then cooled to room temperature, dissolved in 60 ml of THF and the solution was added dropwise to a cooled solution (0° C.) of 2.0 g (13.5 mmol) of the polyester of Example 6 (monomer unit 2c) and 12.3 g (121.5 mmol) of 4-methylmorpholine in 120 ml of tetrahydrofuran-dimethylformamide (5:1). The mixture was stirred for additional 4 hrs. at 0° C., then the solvent was evaporated under reduced pressure and the residue was dissolved in 500 ml of dichloromethane. The dichloromethane solution was washed twice with water, dried over anhydrous sodium sulphate and the solvent was evaporated under reduced pressure. The polymeric product was precipitated twice by dissolving in 35 ml of dichloromethane and dropwise addition of the dichloromethane solution to 1500 ml of t-butyl methyl ether to give, after drying in vacuo for 48 hrs., a polyester having the monomer unit 10c as a brownish-yellow powder.

$\eta_{inh}$(dl/g)=0.07 in $CHCl_3$
Mw=9370 Da, Mn=4690 Da, Mw/Mn=2.0
Tg=51° C.
IR (KBr): Strong absorptions at 1756, 1689, 1243, 1194, 1172 and 981 $cm^{-1}$.
$^1$H-NMR ($CDCl_3$, 360 MHz): δ=4.36–4.47 ppm (m, 2H, $2H_B$ of $2CH_2$); 4.58–4.69 (m, 2H, $2H_A$ of $2CH_2$); 5.755 (m, 2H, 2CH); 7.39 (m, 4H, 4 arom.H); 7.52 (m, 2H, 2 aroma.H); 7.885 (m, 4H, 4 arom.H).
$^{13}$C-NMR (CDCl3, 90 MHz): δ=184.73 ppm (—C(O)—); 162.48 (—C(O)—O); 153.93 (O—C(O)—O); 135.12 (arom. CH) 131.73 (arom. C); 129.94 (arom. CH); 128.93 (arom. CH); 70.43 (O—CH); 65.48 (O—$CH_2$).
Microanalysis: Calculated for $C_{21}H_{16}O_9$: C 61.18%, H 3.88% found: 60.60%, 4.30%

EXAMPLE 17
Synthesis of the Polyester Having the Monomer Unit 11c 30.4 g (264 mmol) of dichloromethyl methyl ether were added slowly to 34.4 g (264 mmol) of 4-methyl-2-oxovaleric acid and the mixture was heated to 50° C. (bath temp.). After stirring for 60 min. at this temperature, the crude product was fractionated on a vigreux column to give the 4-methyl-2-oxovaleryl chloride (b.p. 41° C./14 mbar). 14.7 g (99 mmol) of 4-methyl-2-oxovaleryl chloride were dissolved in 144 ml of tetrahydrofuran and the solution was added dropwise at 0° C. to a solution of 6.66 g (45 mmol) of the polyester of Example 6 (monomer unit 2c) and 7.83 g (99 mmol) of pyridine in 514 ml of tetrahydrofuran/dimethylformamide (5:1). The reaction mixture was stirred at 0° C. for additional 3 hours, then filtered through Hyflo Cel and the filtrate was concentrated under reduced pressure. The polymeric product was precipitated by dropwise addition of the resulting solution into 1000 ml of isopropyl ether/n-hexane (1.5:1). The precipitate was stirred several times in tetrahydrofuran/diethyl ether (1:2) and the insoluble part was removed by filtration. The resulting clear solution was added dropwise into 500 ml of isopropyl ether, the precipitate was redissolved in tetrahydrofuran and precipitated from 1000 ml of n-hexane giving a polyester having the monomer unit 11c.

$\eta_{inh}$(dl/g)=0.10 in $CHCl_3$
Mw=15300 Da, Mn=9050 Da, Mw/Mn=1.69
Tg=30.3° C.
IR (KBr): Strong absorptions at 1763, 1740, 1248 and 1047 $cm^{-1}$.
$^1$H-NMR ($CDCl_3$, 360 MHz): δ=0.952 ppm (d, J=6.5 Hz, 12H, $4CH_3$); 2.16 (sept., J=6.5 Hz, 2H, 2 side chain CH); 2.705 (d, J=6.5 Hz, 4 H, 2 side chain $CH_2$); 4.30 (m, 2 H, 2 $H_B$ of 2 $CH_2$); 4.522 (dm, J=ca. 12 Hz, 2 H, 2 $H_A$ of 2 $CH_2$); 5.453 (m, 2 H, 2 CH).
$^{13}$C-NMR ($CDCl_3$, 90 MHz): δ=192.42 ppm (—C(O)—); 59.96 (—C(O)—O); 154.00 (O—C(O)—O); 70.45 (CH); 65.12 ($CH_2$); 47.85 (side chain $CH_2$); 24.13 (side chain CH); 22.38 ($CH_3$).

EXAMPLE 18

Synthesis of the polyester having the monomer unit 12c 2.96 g (20 mmol) of the polyester having the monomer unit 2c (of Example 6) was dissolved in 15 ml of dimethylformamide, the solution was diluted with 80 ml tetrahydrofuran and cooled to 0° C. in an ice bath. 3.16 g (40 mmol) pyridine and a solution of 5.99 g (44 mmol) Ethyl oxalyl chloride in 40 ml of tetrahydrofuran were added subsequently and dropwise over 15 minutes to the stirred solution at 0° C. The reaction mixture was stirred for additional 7 hours at this temperature, then dissolved in 300 ml of dichloromethane and the dichloromethane solution was washed with aqueous 5% sodium bicarbonate (2x) and water. The organic layer was dried over anhydrous sodium sulfate, the solvent was evaporated under reduced pressure and the residue was dissolved in 20 ml of dichloromethane. The product was precipitated by dropwise addition of the dichloromethane solution to 1500 ml diethyl ether.

The precipitate was dried in vacuo for 48 hours at room temperature to give the polyester.

$\eta_{inh}$(dl/g)=0.09 in $CHCl_3$
Mw=15000 Da, Mn=9850 Da, Mw/$M_,$=1.52
Tg=58.8° C.
IR (KBr): Strong absorptions at 1779, 1749, 1313, 1249, 1181 and 1155 $cm^{-1}$.
$^1$H-NMR ($CDCl_3$, 360 MHz): δ=1.364 ppm (t, $^3$J=ca.7 Hz, 6H, $2CH_3$); 4.346 (q,$^3$J=ca.7 Hz, 4H, 2 ethyl $CH_2$); 4.295–4.410 (m, 2H, $2H_B$ of 2 $CH_2$); 4.475–4.575 (m, 2H, $2H_A$ of 2 $CH_2$).
$^{13}$C-NMR ($CDCl_3$, 90 MHz): δ=156.69 ppm (—C(O)—O); 156.59 (—C(O)—O); 153.88 (O—C(O)—O); 71.09 (CH); 65.01 ($CH_2$); 63.48 ($CH_2$); 13.84 ($CH_3$).
Microanalysis: Calc. for $C_{13}H_{16}O_{11}$: C 44.85%, H 4.60% found: 44.70%, 4.80%

EXAMPLE 19

Synthesis of the polyester having the monomer unit 13c 5.18 g (35 mmol) of the polyester having the monomer unit 2c (of Example 6) were suspended in 250 ml of tetrahydrofuran. 7.1 ml (6.958 g; 88 mmol) of pyridine and 51 ml (57.22 g; 353 mmol) of diethyl pyrocarbonate were added while under argon. A gentle evolution of $CO_2$ started simultaneously on addition of diethyl pyrocarbonate. The mixture was stirred for 3 hours at room temperature, after which time the evolution of $CO_2$ was slowed down. The solvent was then evaporated at reduced pressure at 30° C., the residue was dissolved in 25 ml of dichloromethane and the product was precipitated on dropwise addition of the dichloromethane solution into 1000 ml of hexane. The precipitate was redissolved in 25 ml of dichloromethane and reprecipitated from 1500 ml of diethyl ether/hexane (2:1). The precipitate was dried in vacuo for 48 hours to give the polyester.

$\eta_{inh}$(dl/g)=0.12 in $CHCl_3$
Mw=15650 Da, Mn=10550 Da, Mw/Mn=1.48
Tg=49.8° C.
IR (KBr): Strong absorptions at 1752 and 1245 $cm^{-1}$.
$^1$H-NMR ($CDCl_3$, 360 MHz): δ=1.315 ppm (t, J=ca.7 Hz, 6H, $2CH_3$); 4.222 (q, J=ca.7 Hz, 2 $CH_2$); 4.16–4.32 (m, 2H, $2H_B$ of 2 chain $CH_2$); 4.42–4.52 (m, 2H, $2H_A$ of 2 chain $CH_3$); 5.175 (m, 2H, 2CH).
$^{13}$C-NMR ($CDCl_3$, 90 MHz): δ=154.13 ppm (O—C(O)—O); 72.43 and 72.38 (CH); 65.47 ($CH_2$); 64.81 ($CH_2$); 14.11 ($CH_3$).
Microanalysis: Calc. for $C_9H_{12}O_7$: C 45.21%, H 5.52% found: 45.50%, 5.60%

EXAMPLE 20

Synthesis of the polyester having the monomer unit 14c 2.96 g (20 mmol) of the polyester having the monomer unit 2c (of Example 6) were suspended in 150 ml of tetrahydrofuran. 3.3 ml (3.2 g; 41 mmol) of pyridine and 5.8 ml (6.5 g; 40 mmol) of diethyl pyrocarbonate were added while under argon. A gentle evolution of $CO_2$ started simultaneously on addition of diethyl pyrocarbonate. The mixture was stirred for 30 min. at room temperature, then the solvent was evaporated at reduced pressure at 30° C. and the residue was dissolved in 25 ml of dichloromethane. The product was precipitated on dropwise addition of the dichloromethane solution to 1500 ml of diethylether. The precipitate was dried in vacuo for 48 hours to give the polyester, in which according to $^1$H-NMR ca. 76.5% of the hydroxyl groups were ethoxycarbonylated and ca. 23.5% were in free condition. Thus the ratio of di-ethoxycarbonylated units to mono-ethoxycarbonylated units was ca. 53% : 47%, according to the integral ratio of the signals at 5.18 ppm (m, 2 CH of di-ethoxycarbonylated units) and 5.02 ppm (m, 1 CH of mono-ethoxycarbonylated units).

$\eta_{inh}$(dl/g)=0.10 in $CHCl_3$

Mw=11450 Da, Mn=7950 Da, Mw/Mn=1.44

Tg=45.4° C.

IR (KBr): 3508 (OH-Absorption) and strong absorptions at 1757, 1234, 1005 and 786 $cm^{-1}$.

$^1$H-NMR ($CDCl_3$, 360 MHz): $\delta$=1.312 ppm (t, $^3$J=ca. 7.2 Hz, $2CH_3$ of di-units and $1CH_3$ of mono-units); 2.75–3.35 (m, OH of mono-units); 4.22 (q, $^3$J=ca.7.2 Hz, $2CH_2$ of di-units and $1CH_2$ of mono-units); 4.08–4.40 (m, 2H of di-units and 4H of mono-units); 4.40–4.54 (m, 2H of di-units and 1H of mono-units); 5.02 (m, 1CH of mono-units); 5.18 (m, 2CH of di-units).

EXAMPLE 21

Synthesis of the polyester having the monomer unit 15c 1.48 g (10 mmol) of the polyester having the monomer unit 2c (of Example 6) were suspended in 80 ml of toluene and the suspension was stirred for 1 hr. at room temperature. After the addition of 1.76 g (22 mmol) pyridine, a solution of 9.88 g (22 mmol) cholesteryl chloroformate in 70 ml of toluene was added dropwise over 10 min. to the stirred suspension and stirring was continued at room temperature for 50 hrs. The reaction mixture was then dissolved in 400 ml of dichloromethane, the dichloromethane solution was washed with aqueous 5% sodium bicarbonate (2x) and with water, and dried over anhydrous sodium sulfate. Then, the solvent was evaporated under reduced pressure, the residue was dissolved in ca. 50 ml of dichloromethane and the product was precipitated on dropwise addition of the dichloromethane solution into 2000 ml of 2-propanol. The product was further purified by dissolution in 50 ml of dichloromethane and precipitation from 1000 ml of n-butanol. The fine, powdery polyester was isolated by filtration and dried in vacuo for 48 hrs.

$\eta_{inh}$(dl/g)=0.12 in $CHCl_3$

Mw=18150, Mn=11600, Mw/Mn=1.56

Tg=No Tg was observable from −30° C. to +240° C.

IR (KBr): Strong absorptions at 2951, 1758 and 1249 $cm^{-1}$.

$^1$H-NMR ($CDCl_3$, 360 MHz): $\delta$=0.684 ppm (s, 6H, $2CH_3$); 0.869 (d.d, $^3$J=ca. 6.5 Hz, 12H, $4CH_3$); 0.921 (d, $^3$J=ca. 6.2 Hz, 6H, $2CH_3$); 1.083 (s, 6H $2CH_3$); 0.75–2.10 (m, 52H, various $CH_2$ and CH); 2.28–2.47 (m, 4H, $2CH_2$); 4.241 (m, 2H, $2H_B$ of 2 chain $CH_2$); 4.40–4.55 (m, 4H, $2H_A$ of 2 chain $CH_2$ and 2CH of cholesteryl residue); 5.153 (m, 2H, 2 chain CH); 5.396 (m, 2H, 2 olefin H).

EXAMPLE 22

Synthesis of the polyester having the monomer unit 16c 2.96 g (20 mmol) of the polyester having the monomer unit 2c (of Example 6) were suspended in 150 ml of toluene and the suspension was stirred for 1 hr. at room temperature. After the addition of 3.48 g (44 mmol) of pyridine, a solution of 10.68 g (50 mmol) 4-methoxycarbonylphenyl chloroformate in 50 ml of toluene was added to the stirred suspension over 15 min. and the reaction mixture was stirred for additional 65 hrs. at room temperature. Then, the solvent was evaporated at reduced pressure, the residue was diluted with dichloromethane and the dichloromethane solution was washed with aqueous 5% sodium bicarbonate (2x) and water. The organic layer was then dried over anhydrous sodium sulfate, filtered and the solvent was evaporated at reduced pressure. The residue was dissolved in 50 ml of dichloromethane and the product was precipitated by dropwise addition of the dichloromethane solution to 1000 ml of diethyl ether. The precipitated polyester was redissolved in 50 ml of dichloromethane, reprecipitated from 1000 ml ethanol and dried in vacuo for 48 hrs.

$\eta_{inh}$(dl/g)=0.12 in $CHCl_3$

Mw=22600 Da, Mn=13500 Da, Mw/Mn=1.67

Tg=90.9° C.

IR (KBr): Strong absorptions at 1772, 1723, 1282, 1235, 1211 and 1112 $cm^{-1}$.

$^1$H-NMR ($CDCl_3$, 360 MHz): $\delta$=ca. 3.86 ppm (broad s, 6H, $2CH_3$); 4.28–4.45 (m, 2H, $2H_B$ of 2 $CH_2$); 4.64 (m, 2H, $2H_A$ of 2 $CH_2$); 5.319 (m, 2H, 2CH); 7.18–7.30 (m, 4H, 4 arom. H); 7.95–8.09 (m, 4H, 4 arom. H).

$^{13}$C-NMR ($CDCl_3$, 90 MHz): $\delta$=165.85 ppm (—C(O)—O); 154.23 (arom. C); 154.04 (O—C(O)—O); 152.19 (O—C(O)—O); 131.22 (arom.CH); 128.20 (arom. CH); C); 120.73 (arom. 73.50 (CH—O); 65.32 ($CH_2$—O); 52.19 ($CH_3$).

EXAMPLE 23

Synthesis of the polyester in which the monomer unit is 17c 2.0 g (13.5 mmol) of the polyester of Example 6 (monomer unit 2c) were suspended in 120 ml of tetrahydrofuran 24.2 g (203 mmol) of phenyl isocyanate and 0.5 ml of pyridine were added under an argon stream and the mixture was stirred for 96 hrs. at room temperature. The product was then precipitated by dropwise addition of the solution to 1500 ml of hexane. The precipitate was dissolved in 20 ml of tetrahydrofuran and the solution was added dropwise to 500 ml of diethyl ether. The reprecipitation from tetrahydrofuran-diethyl ether was repeated once again and the product was dried in vacuo at room temperature for 48 hrs. to yield a polyester having the monomer unit 17c. According to $^1$H-NMR, the product comprised 7% free hydroxyl groups, whilst the remainder 95% of the hydroxyl groups were derivatized as carbamate ester.

Thus, the product comprised 86% di-carbamoylated units (di-units) and 14% mono-carbamolyated units (mono-units). The ratio of mono-carbamoylation and di-carbamoylation was determined from the integrals of the signals at 5.04 ppm (1 CH of mono-units) and 5.30 ppm (2 CH of di-units).

$\eta_{inh}$ (dl/g)=0.115 in acetone

Mw=17700 Da, Mn=10900 Da, Mw/Mn=1.62

Tg=86.7° C.

IR (KBr): Strong absorptions at 1744, 1602, 1530, 1446 and 1211 cm$^{-1}$.

$^1$H-NMR (d$_6$-DMSO, 360 MHz): δ=3.85–4.50 ppm (m, 1 CH and 2 CH$_2$ of mono-units and 2 CH$_2$ of di-units); 5.04 (1 CH of mono-units); 5.30 (m, 2 CH of di-units); 5.63 (m, OH of mono-units); 6.96 (m, 2 arom. H); 7.23 (m, 4 arom. H); 7.44 (m, 4H, 4 arom.H); ca. 9.80 (m, 2 NH).

$^{13}$C-NMR (d$_6$-DMSO, 90 MHz): δ=ca. 154.0 ppm (multiple signal; O—C(O)—O); 152.5 (O—C(O)—NH); 138.6 (C(1')); 128.6 (C(3')); 122.7 (C(4')); 118.5 (C(2')); ca. 69.5 (broad, CH); ca. 66.5 (broad, CH$_2$). Some additional, weak signals of the minor mono-carbamoylated units are also present.

EXAMPLE 24

Synthesis of the polyester having the monomer unit 18c 444 mg (3 mmol) of polyester having the monomer unit 2c of example 6 was dissolved in 8 ml of dimethylformamide. The solution was diluted with 32 ml of tetrahydrofuran. To the stirred solution subsequently were added at room temperature 4.78 g (18 mmol) of BOC-L-phenylalanine, 3.71 g (18 mmol) of N,N'-dicyclohexylscarbodiimide and 135 mg (1.2 mmol) of 4-dimethylaminopyridine. The mixture was stirred for additional 2 hours at room temperature. After filtration of the formed suspension, the solvent was evaporated under reduced pressure, the residue was dissolved in dichloromethane and the solution was washed subsequently with water, aqueous 1M acetic acid, 5% sodium hydrogencarbonate and saturated brine. The dichloromethane solution was then dried on anhydrous sodium sulfate and evaporated to a final volume of ca. 20 ml. By dropwise addition of this solution into 200 ml of hexane a precipitate was formed. The solid product was reprecipitated from dichloromethane/hexane and dried in vacuo to give the polyester of which the amino groups are protected by tert.-butyloxycarbonyl groups.

$\eta_{inh.}$ (dl/g)=0.09 in CHCl$_3$

Mw=15000 Da, Mn=10800 Da, Mw/Mn=1.39

Tg=82.4° C.

IR (KBr): Strong absorptions at 1760, 1717, 1499, 1251 and 1166 cm$^{-1}$.

$^1$H-NMR (d$_6$-DMSO, 360 MHz): δ=1.18 ppm (m, 18H, 6CH$_3$); 2.78–294 (m,2H), 2 side chain CH$_2$); 4.04–4.30 (m,6H, 2 chain CH$_2$ and 2 side chain CH); 5.24–5.50 (m,2H, 2 chain CH); 7.12–7.38 (m,12H, 2NH and 10 arom. H).

$^{13}$C-NMR (d$_6$-DMSO, 90 MHz): δ=171.49 and 171.04 ppm (—C(O)—O); 155.34 and 155.24 (O—C(O)—O); 153.60 (NH—C(O)—); 137.22 (arom. C); 128.93, 128.04 and 126.34 (arom. CH); 78.38 and 78.31 (side chain C); 69.07 (chain CH); 65.43 (chain CH$_2$); 55.05 (side chain CH); 36.2 and 35.9 (benzyl CH$_2$); 28.0 (CH$_3$).

Microanalysis: Calculated for C$_{33}$H$_{42}$N$_2$O$_{11}$: C 61.67% H$_{6.59}$% N 4.36% found: 61.40% 6.40% 4.30%

The tert.-butyloxycarbonyl protecting groups are removed by known methods, e.g. by treatment of the product with an acid, e.g. trifluoroacetic acid, to give the trifluoroacetate salt or, after neutralisation, to give the polyester with free amino groups.

Polyesters having monomer units 2a–2c are alternatively derivatized with amino acid ester residues by treatment with their corresponding isocyanates. Amino groups of amino acid ester are readily converted into isocyanates: [31]: Japanese Patent 53018515 (1978) and [32]; Shoichiro Ozaki et al., Bull. Chem. Soc. Jpn. 50, 2406 (1977). Subsequent treatment of the isocyanates according to the procedure described in example 23 leads to the formation of the carbamic acid esters of the corresponding amino acid residues.

EXAMPLE 25

Synthesis of the Polyester having the monomer unit 19c 444 mg (3 mmol) of polyester having the monomer unit 2c from example 6 was dissolved in 8 ml of dimethylformamide. The solution was diluted with 32 ml of tetrahydrofuran. To the solution were added subsequently 4.78 g (18 mmol) of Z-L-leucine, 3.71 g (18 mmol) of N,N'-dicyclohexylcarbodiimide and 135 mg (1.2 mmol) of 4-dimethylaminopyridine. The mixture was stirred for 2 hours at room temperature. After filtration of the formed suspension, the solvent was evaporated under reduced pressure, the residue was dissolved in dichloromethane and the solution was washed subsequently with water, aqueous 1M acetic acid, 5% sodium hydrogencarbonate and saturated brine. The dichloromethane solution was then dried on anhydrous sodium sulfate and evaporated to a final volume of ca. 20 ml. By dropwise addition of this solution to 200 ml of hexane a precipitate is formed. The solid product was reprecipitated from dichloromethane/isopropyl ether and dried in vacuo to give the polyester, in which the amino groups are protected by benzyloxycarbonyl groups (Z-group).

Mw=15000, Mw=10800, Mw/Mn=1.39

IR (KBr): Strong absorptions at 2960, 1760, 1723, 1529, 1264 and 1048 cm$^{-1}$.

1H-NMR (d$_6$-DMSO, 360 MHz): δ=0.70–0.97 ppm (m, 12H, 2CH$_3$); 1.34–1.70 (m,6H, 2 side chain CH$_2$ and 2 side chain CH); 4.00–4.30 (m,6H, 2 chain CH$_2$ and 2 side chain CH); 5.00 (m,4H, 2benzyl CH$_2$); 5.32 (m, 2H, 2 chain CH); 7.18–7.42 (m,10H, 10 arom, CH); 7.19 (m,2H, 2NH).

$^{13}$C-NMR (d$_6$-DMSO, 90 MHz): δ=172.18 and 171.70 ppm (—C(O)—O); 155.99 (O—C(O)—O), 153.54 (NH—C(O)—O), 136.66 (arom. C); 128.18, 127.84 and 127.65 (arom. CH); 69.20 (CH); 65.56 (CH$_2$); 52.28 (CH); 24.16 (CH); 22.70, 22.51, 21.19 and 20.96 (CH$_3$).

The esterification was also performed using 2-L-leucyl-L-alanine, under the same reaction conditions to give the corresponding dipeptide ester derivative.

The benzyloxycarbonyl protecting groups are removed by known methods, e.g. by hydrogenation on palladium/charcoal, to give a polyester with free amino groups or, if an acid is added, the corresponding ammonium salt.

EXAMPLE 26

Synthesis of the polyester in which the monomer unit is 20 c 2.5 ml of trifluoroacetic acid and 29 g (150 mmol) of tetraethyl orthocarbonate were added at room temperature to a suspension of 2.22 g (15 mmol) of the polyester of Example 6 (monomer unit 2c) in 150 ml of tetrahydrofuran under an argon stream. The mixture was stirred for 18 hrs. at room temperature. The resulting solution was treated with 3.5 g of powdered sodium bicarbonate, stirred for 30 min. and after filtration, the solvent was evaporated under reduced pressure. The residue was dissolved in 300 ml of dichloromethane and the dichloromethane solution was washed with 300 ml of aqueous 5% sodium bicarbonate by stirring for 15 min. at room temperature. The organic layer was separated, dried over anhydrous sodium sulfate, concentrated to a final volume of ca. 20 ml and the product was precipitated by dropwise addition of the solution to 1000 ml of hexane. The precipitate was dried in vacuo for 48 hrs. at room temperature to yield a polyester having the monomer unit 20c.

$\eta_{inh}$ (dl/g)=0.1 in CHCl$_3$

Mw=11750 Da, Mn=7750 Da, Mw/Mn=1.52

Tg=10.8° C.

IR (film): Strong absorptions at 2982, 1755, 1266, 1214, 1145 and 1047 cm$^{-1}$.

$^1$H-NMR (CDCl$_3$, 360 MHz): δ=1.21 ppm (t, $^3$J=7 Hz, 6 H, 2 CH$_3$); 3.715 (q, $^3$J=7 Hz, 4 H, 2 side chain CH$_2$); 4.27 (m, 2 H, 2 H$_B$ of 2 CH$_2$); 4.315 (m, 4 H, 2 H$_A$ of 2 CH$_2$ and 2 CH);

$^{13}$C-NMR (CDCl$_3$, 90 MHz): δ=154.39 ppm (O—C(O)—O); 127.48 (Orthocarbonate C); 74.74 (CH); 67.38 (CH$_2$); 60.16 (side chain CH$_2$); 14.98 (CH$_3$).

Microanalysis : Calculated for C$_{10}$H$_{16}$O$_7$: C 48.39%, H6.50% found: 48.10%, H6.50%

EXAMPLE 27

Synthesis of the polyester in which the monomer unit is 21c 2.5 ml of trifluoroacetic acid and 44.5 g (300 mmol) of triethyl orthoformate were added at room temperature under an argon stream to a suspension of 4.44 g (30 mmol) of the polyester of Example 6 (monomer unit 2c) in 300 ml of tetrahydrofuran. The mixture was stirred for 4 hrs. at room temperature, the resulting solution was treated with 4.5 g of powdered sodium bicarbonate, stirred for another 30 min. at room temperature and after filtration, the solvent was evaporated under reduced pressure. The residue was dissolved in 300 ml of dichloromethane and the solution was washed with 300 ml of aqueous 5% sodium bicarbonate by stirring for 15 min. at room temperature. The organic layer was separated, dried over anhydrous sodium sulfate and concentrated to a final volume of ca. 50 ml. The product was then precipitated by dropwise addition of the solution to 1200 ml of hexane. The product was reprecipitated by dissolving in 15 ml of dichloromethane and dropwise addition of the solution to 500 ml of isopropyl ether. The reprecipitation was repeated and the product was dried in vacuo for 48 hrs. at room temperature to give a polyester having the monomer unit 21c.

$\eta_{inh}$(dl/g)=0.10 in CHCl$_3$

Mw=10650 Da, Mn=6650 Da, Mw/Mn=1.60

Tg=23.5° C.

IR (Film): Strong absorption at 1753, 1263 and 1069 cm$^{-1}$. $^1$H-NMR (CDCl$_2$, 360 MHz): δ=1.217 ppm (t, $^3$J=7 Hz, 3 H, CH$_3$); 3.60 (q, $^3$H=7 Hz, 2 H, side chain CH$_2$); 4.15–4.40 (m, 6 H, 2 CH$_2$ and 2 CH); 5.87 (s, 1 H, side chain CH).

$^{13}$C-NMR (CDCl$_3$, 90 MHz): δ=154.43 (O—C(O)—O); 115.93 (ortho ester CH); 75.05 (CH); 68.22 (CH$_2$); 66.93 (CH$_2$); 60.77 (side chain CH$_2$); 14.96 (CH$_3$).

Microanalysis: Calculated for C$_8$H$_{12}$O$_6$: C 47.06%, H 5.92% found: 46.70%, 6.00%

EXAMPLE 28 a) Synthesis of 2,3:4,5- and 2,4:3,5-di-O-Isopropylidene-D-mannitol 273.5 g (1.37 mol) of 1,6di-O-benzoyl-D-mannitol (Ref: [28]) and 2.7 g of p-toluenesulfonic acid were suspended in 1650 g (16 mol) of 2,2-dimethoxypropane and the mixture was heated to reflux for 1 hour. After cooling to room temperature, the solution was diluted with diethyl ether, washed twice with aqueous 5% sulfuric acid and with saturated NaCl-solution, dried over anhydrous sodium sulfate and evaporated under reduced pressure to yield a crude product, being mainly a mixture 3 compounds on TLC.

The crude mixture was dissolved in 5000 ml of chloroform and a solution of 10 g (0.18 mol) sodium methylate in 1500 ml of methanol was added. The mixture was stirred for 20 hrs. at room temperature, then the solvent was evaporated under reduced pressure and the residue was washed several times with light petroleum. The crude product mixture was dissolved in a minimum amount of chloroform and subjected to flash chromatography on silica gel. Elution with diethyl ether containing 0.1% triethylamine gave 45 g of pure 2,4:3,5-di-O-isopropylidene-D-mannitol. Subsequent elution with ethyl acetate and 0.1% triethylamine gave a mixture of 2,4:3,5- and 2,3:4,5-O-isopropylidene-D-mannitol, followed by pure 2,3:4,5-di-O-isopropylidene-D-mannitol. The third, more polar component of the mixture, being presumably 3.4:0-isopropylidene-D-mannitol, was not isolated. The products gave satisfactory spectroscopical data.

b) Polyester from 2,4:3,5-di-O-Isopropylidene-D-Mannitol and diethyl carbonate, having the monomer unit 22b.

5.25 g (20 mmol) of 2,4:3,5-di-O-isopropylidene-D-mannitol was polycondensed with diethyl carbonate according to the procedure described in Example 3) to give the polyester.

$\eta_{inh}$(dl/g)=0.19 in CHCl$_3$

Mw=16000 Da, Mn=11700 Da, Mw/Mn=1.37

Tg=105.6° C.

[alpha]$_D^{-+14.3°}$ (c=1 in CHCl$_3$, 20° C.)

IR (KRb): Strong absorptions at 1756, 1384, 1266, 1219 and 1173 cm$^{-1}$.

$^1$H-NMR (CDCl$_3$, 360 MHz): δ=1.32 ppm (s, 6H, 2CH); 1.39 (s, 6H, 2CH$_3$); 3.80–3.96 (m, 4H, 4CH); 4.22 (d.d, $^2$J$_{AB}$=ca. 11.5 Hz and J=6.2 Hz, 2H$_B$ of 2CH$_2$); 4.28 (d.d, $^2$J$_{AB}$=ca. 11.5 Hz and J=2.7 Hz, 2H$_A$ of 2CH$_2$).

$^{13}$C-NMR (CDCl$_3$, 90 MHz): δ=155.02 ppm (O—C(O)—O); 101.14 (O—C—O); 67.88 and 67.76 (CH); 67.54 (CH$_2$); 27.55 and 23.64 (CH$_3$).

Microanalysis: Calc. for C$_{13}$H$_{20}$O$_7$: C 54.19%, H 6.94% found: 54.00%, 7.10%

EXAMPLE 29

Polyester from 2,3:4,5-di-O-Isopropylidene-D-mannitol and Diethyl carbonate, having the monomer unit 23b:

10.5 g (40 mmol) of 2,3:4,5-di-O-Isopropylidene-d-mannitol (see Example 28a) was polycondensed with diethyl carbonate according to the procedure described in example 3) to give the polyester.

$\eta_{inh}$(dl/g): 0.185 in CHCl$_3$

Mw=20500 Da, Mn=17700 Da, Mw/Mn=1.16

Tg=80.8° C.

IR (KBr): Strong absorptions at 1758, 1267, 1091 and 972 cm$^{-1}$.

$^1$H-NMR (CDCl$_3$, 360 MHz): δ=1.35 ppm (s, 6H, 2CH$_3$); 1.495 (s, 6H, 2CH$_3$); 4.22–4.37 (m, 6H); 4.38–4.47 (m, 2H).

$^{13}$C-NMR (CDCl$_3$, 90 MHz): δ=154.53 ppm (O—C(O)—O); 109.59 (acetal C); 74.67 (CH); 74.10 (CH); 67.07 (CH$_2$); 27.18 (CH$_3$); 25.38 (CH$_3$);

Microanalysis: Calculated for $C_{13}H_{20}O_7$: C 54.19%, H 6.94% found: 53.50% 6.90%

EXAMPLE 30

Synthesis of the polyester having the monomer unit 24b 5.0 g (17.3 mmol) of the polyester having the monomer unit 22b (different batch with Mw=6650 Da and Mw=5270 Da) were hydrolysed with 46 ml of trifluoroacetic acid and 7 ml of water in 46 ml dichloromethane, according to the procedure described in Example 4, to give the polyester.

$\eta_{inh}$(dl/g)=0.07 in $H_2O$

Tg=47.2 and 58.9° C. (from the 1, run)

IR (KBr): Strong absorptions at 3408, 1741, 1282 and 10174 $cm^{-1}$.

$^1$H-NMR ($d_6$-DMSO, 360 MHz): δ=3.59 ppm (d, J=9 Hz, 2 H, 2CH); 3.68 (m, 2 H, 2 CH); 4.07 (m, 2H, 2 $H_B$ of 2 $CH_2$); 4.33 (d, J=10.5 Hz, 2 H, 2 $H_A$ of 2 $CH_2$); 2.8–4.8 (broad m, 4 H, 4 OH).

$^{13}$C-NMR ($d_6$-DMSO, 90 MHz): δ=155.16 ppm (O—C (O)—O); 70.36 ($CH_2$); 68.72 (CH); 68.10 (CH).

Microanalysis: Calculated for $C_7H_{12}O_7$: C 40.39%, H 5.81% found: 39.60%, 6.00%

EXAMPLE 31

Synthesis of the polyester having the monomer unit 25b 1.04 g (5 mmol) of the polyester of Example 30 (having the monomer unit 24b) were acetylated according to the procedure described in Example 7, to give the polyester having the monomer unit 25b.

$\eta_{inh}$=0.075 in $CHCl_3$

Mw=6200 Da, Mn=5050 Da, Mw/Mn=1.23

Tg=54.7° C. (from the 1. run)

IR (KBr): Strong absorptions at 1753, 1373, 1268 and 1281 $cm^{-1}$.

$^1$H-NMR ($CDCl_3$, 360 MHz): δ=2.05 ppm (s, 6 H, 2 $CH_3$); 2.09 (s, 6 H, 2 $CH_3$); 4.11 (dd, $^2J_{AB}$=12 Hz and J=5.5 Hz, 2 H, 2 $H_B$ of 2 $CH_3$); 4.24 (dd, $^2J_{AB}$=12 Hz and J=3 Hz, 2 H, 2 $H_A$ of 2 $CH_2$); 5.08 (m, 2 H, 2 CH); 5.41 (d, J=8 hz, 2 H, 2 CH).

$^{13}$C-NMR ($CDCl_3$, 90 MHz): δ=169.72 ppm (—C(O)—O); 169.60 (—C(O)—O); 154.29 (O—C(O)—O); 67.54 (CH); 65.80 ($CH_2$); 20.76 ($CH_3$); 20.53 ($CH_3$).

Microanalysis: Calculated for $C_{15}H_{20}O_{11}$: C 47.88%, H 5.36% found: C 47.50%, H 5.50%

EXAMPLE 32

Synthesis of the end group-stearoylated polyester 26b 2.88 g (10 mmol) of the polyester having monomer unit 22b ($M_2$=6650 Da, $M_n$=5270 Da) were dissolved in 53 ml of tetrahydrofuran and treated subsequently with 0.95 g (12 mmol) pyridine and 1.51 g (5 mmol) stearoyl chloride at room temperature. The reaction mixture was stirred for 20 hours at room temperature, filtered and the product was precipitated by dropwise addition of the filtrate to 500 ml of n-butanol. The product was reprecipitated twice from tetrahydrofuran-/n-butanol and dried in vacuo for 48 hours to yield the end group stearoylated polyester 26b.

The $^1$H-NMR-spectrum of compound 26b clearly showed the presence of a stearate ester function (triplet at 2.33 ppm, J=7.5 Hz, multiplet at 1.59 ppm, singulet at 1.25 ppm and triplet at 0.88 ppm, J=7 Hz) in addition to the monomer unit 22b (showing all characteristic signals of the polyester having the monomer unit 22b). No free stearic acid was detectable in the product).

EXAMPLE 33

Synthesis of the end group-stearoylated polyester 27b 0.85 g of end group-stearoylated polyester 26b was dissolved in 7 ml of dichloromethane and treated subsequently with 7 ml of trifluoroacetic acid and 2.3 ml of water. The solution was stirred for 15 minutes at room temperature and poured slowly into 350 ml of ethyl acetate to precipitate the product. The precipitate was washed well with ethyl acetate and with water and dried in vacuo for 48 hours to obtain the amphiphilic polyester 27b. According to $^1$H-NMR, the product comprised ca. 16 monomer units 24b per stearate ester end group.

This ratio was calculated from the integrals of the signals at 2.28 ppm (t, 2H of the stearate residue) and at 4.34 ppm (d, 2H of the monomer unit 24b). The IR-spectrum (KBr) of 27b showed strong absorptions at 3391, 1740, 1283 and 1076 $cm^{-1}$.

EXAMPLE 34

Polyester from 2-Benzyloxy-1,3-butandiol and Diethyl carbonate, having the monomer unit 28

1.822 g (10 mmol) of 2-benzyloxy-1,3-propanediol were suspended in 7.38 g (62.5 mmol) of diethyl carbonate and 37 mg of di-n-butyl-tin oxide were added while under argon. The mixture was stirred 24 hours at 120° C. and atmospheric pressure, and 24 hours at 130° C./400 mbar, during which time distillation occurs. The distillate was removed while under argon and the mixture was stirred for additional 24 hours at 130° C./5 mbar. The resulting viscous slurry was dissolved in 50 ml of dichloromethane and after removal of the insoluble part by filtration, the solution was evaporated to a final volume of 10 ml. The product was precipitated by dropwise addition of this solution to 200 ml of methanol. The precipitate was further purified by dissolving it in acetone, treatment of this solution with hydrogen peroxide and florisil (magnesium silicate), and working up as described in example 1). Finally, the product was reprecipitated from dichloromethane/methanol to give the polyester having the monomer unit 28, in which the second hydroxyl groups are protected as benzyl ethers.

$\eta_{inh.}$ (dl/g)=0.11 in $CHCl_3$

Mw=9150 Da, Mn=6100 D, Mw/Mn=1.50

Tg=20° C.

IR (film): Strong absorptions at 1751, 1554 and 1239 $cm^{-1}$. $^1$H-NMR ($d_6$-DMSO, 360 MHz): δ=3.88 ppm (m, 1H, CH); 4.165 (d.d, $^2$J=11.5 Hz and $^3$J=5.5 Hz, 2H, 2$H_B$ of 2 $CH_2$); 4.275 (d.d, $^2$J=11.5 Hz and $^3$J=4 Hz, 2H, 2$H_A$ of 2 $CH_2$); 4.565 (s, 2H, benzyl $CH_2$); 7.19–7.33 (m, 5H, arom. CH).

$^{13}$C-NMR ($d_6$-DMSO, 90 MHz): δ=154.14 ppm (O—C(O)—O); 137.87 (arom. C), 128.0 and 127.32 (arom. CH); 73.92 (CH); 70.87 (benzyl $CH_2$); 66.14 (chain $CH_2$).

Microanalysis: Calculated for $C_{11}H_{12}O_4$: C 63.45% H 5.81% found: 63.20% 5.80%

The protecting groups are removed by catalytic hydrogenation on palladium—charcoal to give a polyester with free hydroxyl substituents.

EXAMPLE 35

Co-polyester from 2,3-O-Isopropylidene-L-threitol and 1,4-Butan-diol, having the monomer units 1a and 29

9.73 g (60 mmol) of 2,3-O-Isopropylidene-L-threitol and 5.41 g (60 mmol) of 1,4-Butandiol were added to 45.5 ml of diethyl carbonate. 0.3 g of di-n-butyl-tin-oxide were added to the mixture. The mixture was stirred for 24 hours at 120° C./atmospheric pressure and for another 24 hours at 140° C./400 mbar, during which time distillation occurred. The distillate was then removed and stirring was continued for 24 hours at 140° C./100 mbar and 96 hours at 140° C./1 mbar. The mixture was then allowed to cool to room temperature and the pressure was set to atmospheric pressure. The crude product was dissolved in 50 ml of dichloromethane, the solution was treated with HyfloCel and filtered. The filtrate was evaporated to a final volume of ca. 20 ml and the product was precipitated by dropwise addition of this solution to 500 ml of methanol. The precipitate was further purified by dissolving it in acetone, stirring of the solution with hydrogen peroxide and florisil, and filtration. The solvent was evaporated. The residue was dissolved in dichloromethane and the product was precipitated from methanol. The product, dried in vacuo for 48 hours, gave the co-polyester.

According to $^1$H-NMR, the co-polyester comprised ca. 52.8% of monomer units 29 and 47.2% of monomer units 1a.

This ratio was calculated from the integral ratios of the signals at 1.425 ppm (6H of the monomer unit 1a) and at 1.775 ppm (4H of the monomer unit 29). The remainder protons of both monomer units gave several multiplets between 4.05 and 4.40 ppm (6H of the monomer unit 1a and 4H of the monomer unit 29).

$\eta_{inh.}$ (dl/g): 0.325 in CHCl$_3$
Mw=33600 Da, Mn=18700 Da, Mw/Mn=1.80
Tg=25.7° C.
IR (film): Strong absorptions at 1747 and 1258 cm$^{-1}$.
Microanalysis:
Calculated for $(C_5H_8O_3)_{1.12}$ $(C_8H_{12}O_5)_{1.0}$: C 51.33% H 6.64% found: 51.00% 6.50%

EXAMPLE 36 a) Degradation of polymers in vitro using sterile conditions Polymer samples of compounds having the monomer units 4c, 9c and 11c (implants of 5 mm diameter and 25 mg of weight) were specially dried, weighted, and transfered to glass bottles containing 40 ml phosphate buffered saline sterile buffer (=PBS pH 7.4; ionic strength 0.17) to be shaken at 120 rpm and 37° C. for different times.

At weekly intervals the buffer was replaced by sterile PBS. After selected time points the remaining implant mass was again dried and weighted to determine the mass loss. If possible, the molecular mass of the remaining implant mass was measured using GPC and polystyrene as standard.

Figure 2:
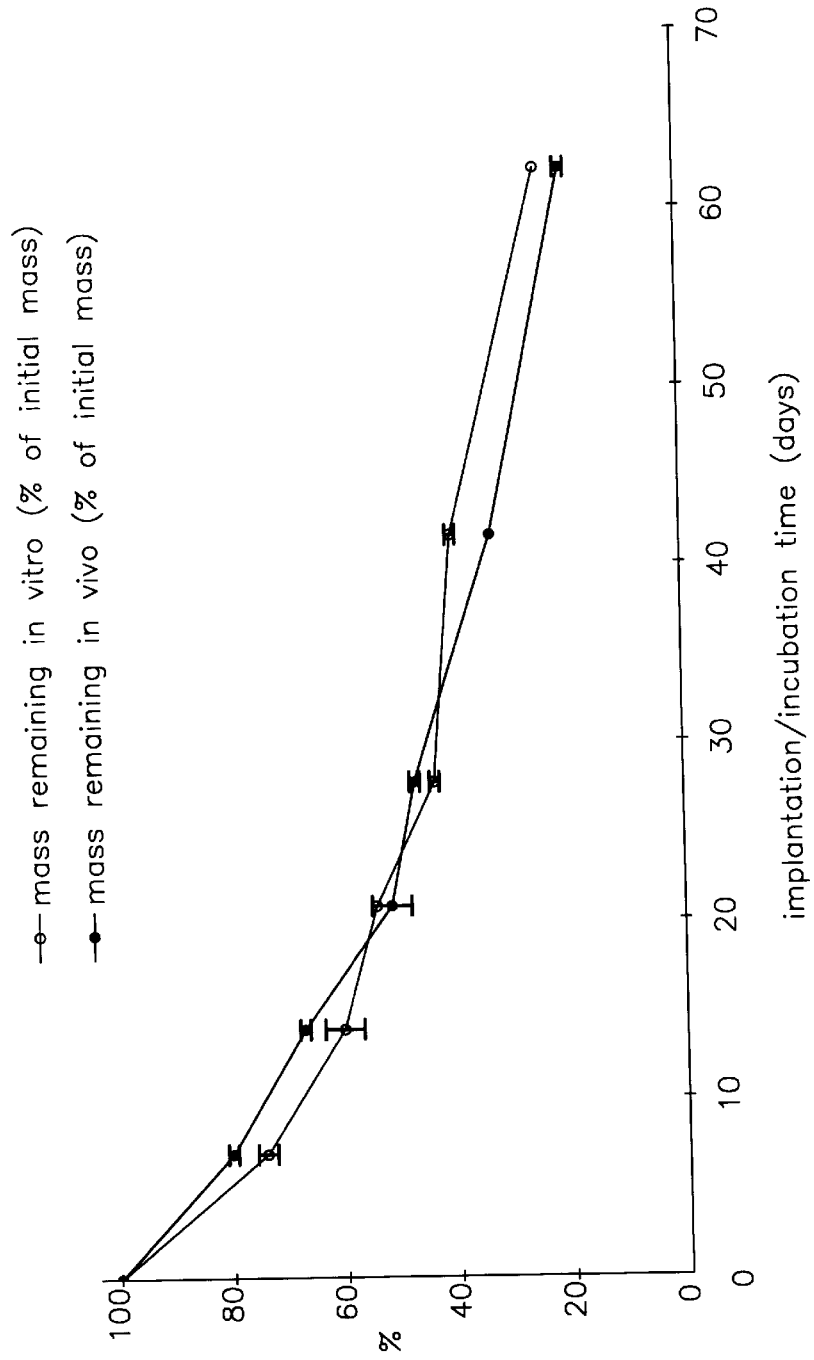
FIG. 2 is a graph of polymer (monomer units 4C) in vitro and in vivo degradation.
Figure 3:
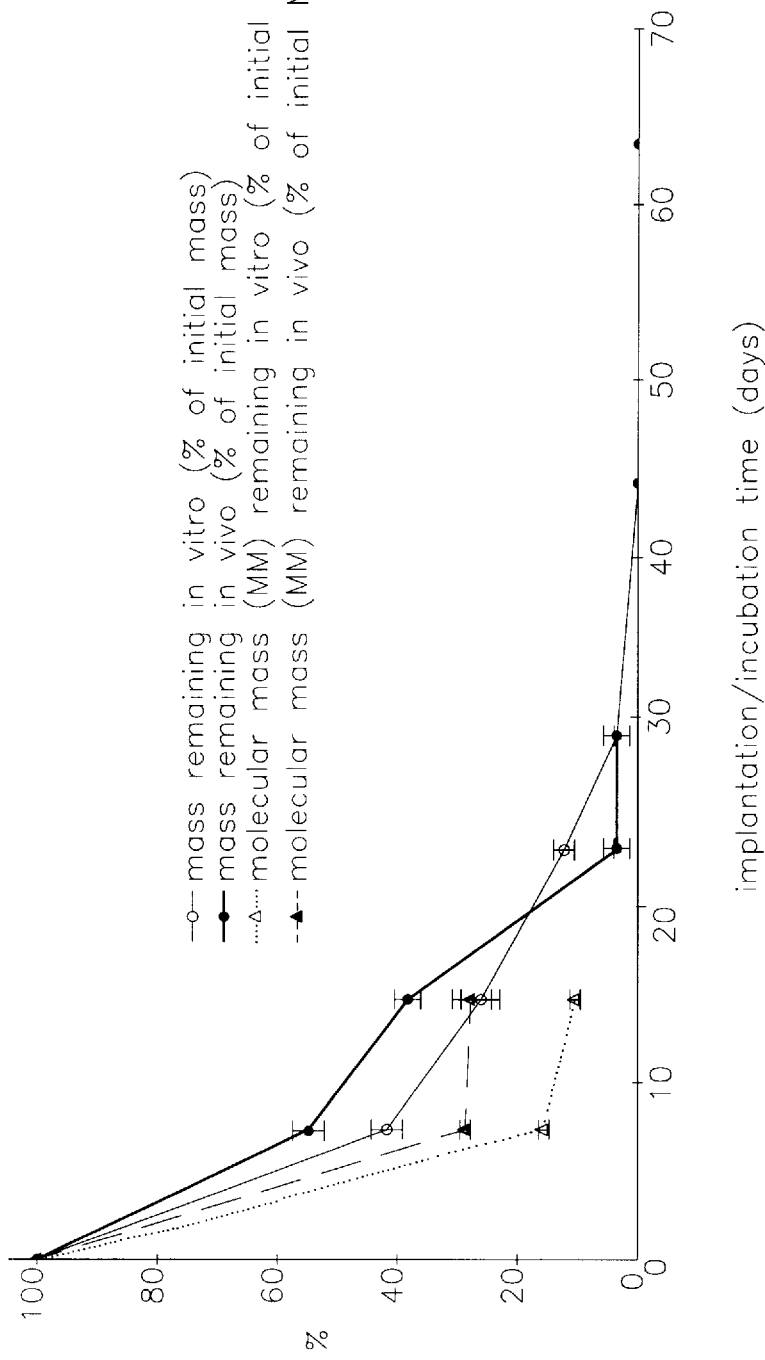
FIG. 3 is a graph of polymer (monomer units 11C) in vitro and in vivo degradation.

The degradation results are shown in FIGS. 1, 2 and 3.

b) Degradation of polymers in rats using sterile conditions To test biodegradation of polymers male Wistar rats (body weight about 250 g) were used having free access to food and drinking water before and during the experiment. The rats were anaesthesized by inhalation of Isofluran (Forene®). Polymer samples of the polyesters having the monomer units 4c and 11c respectively were implanted in subcutaneous skin pouches under laminar flow conditions right or left to the backbone for different times. After specified time points the remaining implant mass was explanted, freed of adhering tissue, dried and weighed to determine mass loss. If possible, molecular mass was determined by GPC using polystyrene as standard.

The degradation results are shown in FIGS. 2 and 3.
Results

The degradation kinetics of polyesters in vitro and in vivo are of a comparable level (FIG. 2 and 3). The time point for complete mass degradation can be varied between 24 hours and about 90 days (FIG. 1 and 2) depending on the chosen structural polyester type.

In some cases the loss of molecular weight is faster than the loss of polyester mass (FIG. 3) which means that first the polyester chains will be cleaved to a certain degree throughout the whole implant, and thereafter water-soluble molecular fragments will be removed.

However, there are also examples of derivatives in which the speeds of the molecule degradation and the removal of water-soluble molecular fragments are more equal (FIG. 1). In these cases, presumably, at each step of hydrolytic degradation a water-soluble fragment is generated, reducing the implant mass and the molecular weight of the remaining polyester.

EXAMPLE 37

Drug compound release from an implant containing the polymer having the monomer units 4c.

For the release octreotide was taken as a drug compound.

Preparation of the implant:

1 g of the polyester was dissolved in 3 ml of methyl acetate. 81.8 mg of Octreotide-pamoate powder (=52.19 mg Octreotide base) was homogeneously suspended in the solution and the solvent was evaporated under reduced pressure.

The residue was milled in a SPEX-mill at the temperature of liquid nitrogen to give a fine powder which was then compressed at 59° C. and 7 bar during 15 min. to implants of 5 diameter and ca. 25 mg of weight.

In vitro degradation of drug loaded polymer implants was measured using the same conditions as described in Example 36a for the unloaded polymer.

Release of octreotide was detected from the buffer solution using HPLC techniques.

Results

The drug compound release correlated with the polymer mass loss in a satisfactory manner, although a very simple technique was used to prepare the implants.

Figure 4:
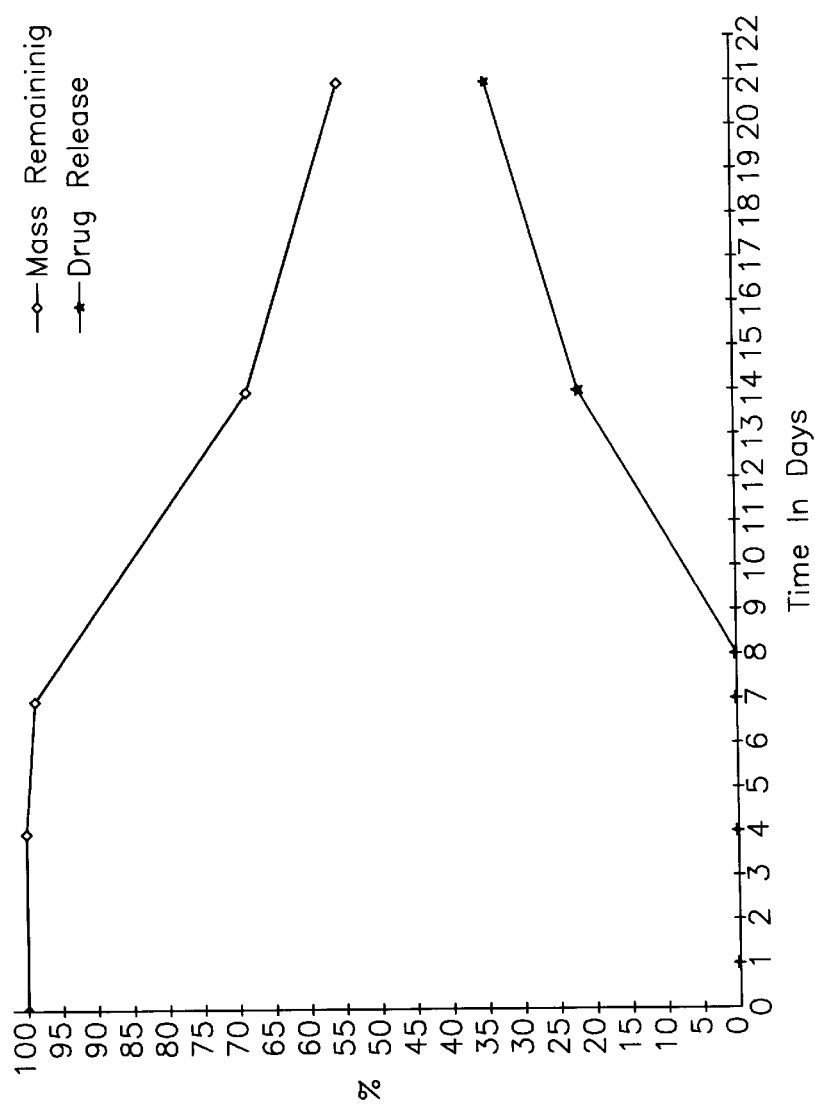
FIG. 4 is a graph of in vitro degradation and drug release from polymer (monomer 4C).

The retardation of the polymer mass loss may be attributed to the presence of the drug compound, since the degradation of the unloaded polymer is faster (see FIG. 4 and 2).

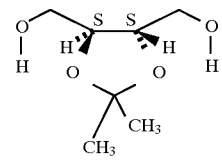

2,3-O-Isopropylidene-L-threitol
(S,S)-Configuration

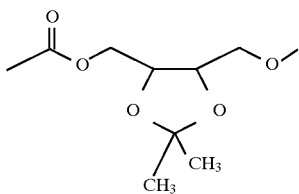

1a (L)
1b (D)
1c (DL)

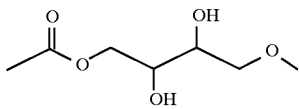

2a (L)
2b (D)
2c (DL)

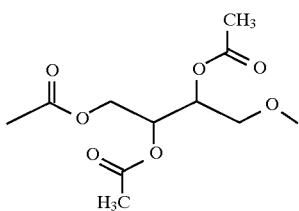

3a (L)
3b (D)
3c (DL)

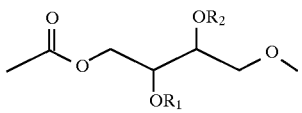

4c: $R_1 = R_2 = -C(=O)H$
5a: $R_1 = -C(=O)-(CH_2)_4-CH_3$
   $R_2 = R_1$ or $H$
6a: $R_1 = -(C=O)-(CH_2)_{16}-CH_3$
   $R_2 = R_1$ or $H$
7c: $R_1 = R_2 = -C(=O)-CH_2-O-CH_2-Ph$
8c: $R_1 = R_2 = -C(=O)-CH_2-OH$

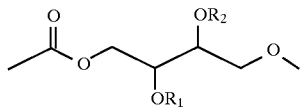

9c: $R_1 = R_2 = -C(=O)-C(=O)-CH_3$
10c: $R_1 = R_2 = -C(=O)-C(=O)-Ph$
11c: $R_1 = R_2 = -C(=O)-C(=O)-CH_2-CH(CH_3)_2$
12c: $R_1 = R_2 = -C(=O)-C(=O)-OCH_2CH_3$
13c: $R_1 = R_2 = -C(=O)-O-CH_2CH_3$
14c: $R_1 = -C(=O)-O-CH_2CH_3$
    $R_2 = R_1$ or $H$
15c: $R_1 = R_2 = -C(=O)-O$-Cholestaryl
16c: $R_1 = R_2 = -C(=O)-O$-(4-Methoxycarbonylphenyl)
17c: $R_1 = -C(=O)-NH-Ph$
    $R_2 = R_1$ or $H$
18c: $R_1 = R_2 = -C(=O)-CH(CH_2Ph)-NH-C(=O)-O-C(CH_3)_3$
19c: $R_1 = R_2 =$
   $-C(=O)-CH(CH_2CH(CH_3)_2)-NH-C(=O)-O-CH_2Ph$

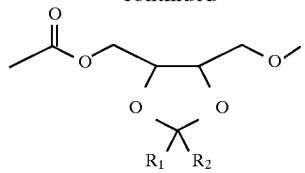

20c: $R_1 = R_2 = O-CH_2CH_3$
21c: $R_1 = H$ and $R_2 = O-CH_2CH_3$

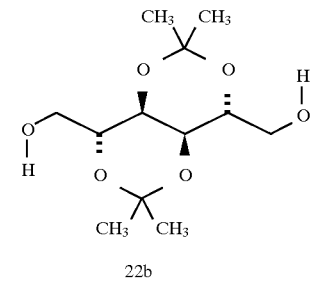

22b

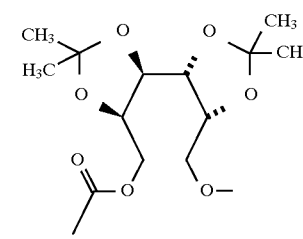

23b

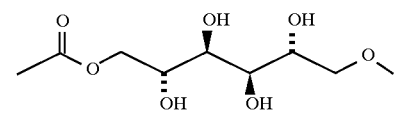

24b

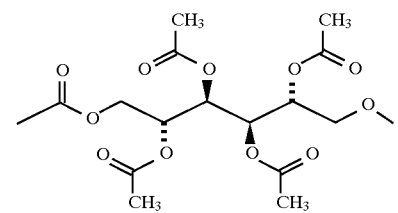

25b

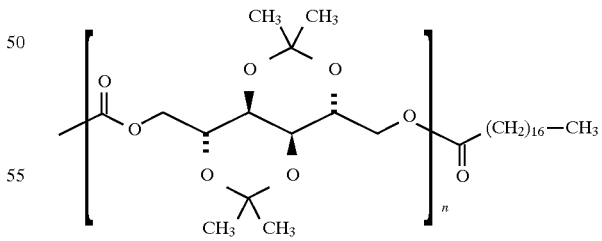

26b

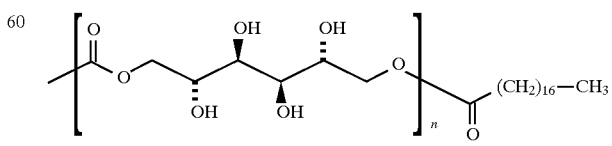

27b

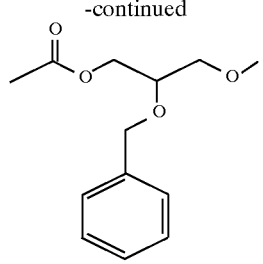

28

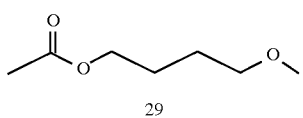

29

I claim:

1. A biodegradable and biocompatible polyester comprising ($C_{3-10}$) alkylene carbonic acid ester units, each alkylene group being a trimethylane group having 1 oxy substituent or a ($C_{4-10}$) alkylene group having 2–8 oxy substituents, each of the oxy substituents occurring independently as a hydroxyl group or independently as a moiety comprising an ester or an ortho ester or an acetal moiety.

2. A polyester according to claim 1, in which all the carbon atoms belonging to the ($C_{2-8}$) alkylene central part of the ($C_{4-10}$) alkylene group are oxysubstituted.

3. A polyester according to claim 1, comprising the alkylene carbonic acid ester units in a randomized copolyester, in a block co-polyester or in homopolyester arrangement.

4. A polyester according to claim 3, in homopolycarbonate arrangement.

5. A polyester according to claim 1 in which the oxy substituent comprises carboxylic acid ester residues.

6. A polyester according to claim 5, in which the carboxylic acid ester residues comprise an oxo carboxylic acid.

7. A polyester according to claim 5, in which the carboxylic acid ester residues comprise a dicarboxylic acid derivative.

8. A polyester according to claim 1 in which the oxy substituent groups comprise carbonic acid ester residues.

9. A polyester according to claim 8 in which the carbonic acid ester residues comprise a hydroxy carboxylic acid derivative.

10. A polyester according to claim 8, in which two oxy substituent comprise a cyclic carbonate residue.

11. A polyester according to claim 1, in which the oxy substituent comprise an acetal or a hemi-acetal residue.

12. A polyester according to claim 1, 5 or 8 in which the oxy substituent comprise an ortho carboxylic acid ester or an ortho carbonic acid ester residue.

13. A polyester according to claim 5 in which the carboxylic acid ester residues comprise those of formic acid of saturated or unsaturated ($C_{2-20}$) fatty acid, or of formic acid and a saturated or unsaturated ($C_{2-20}$) fatty acid.

14. A polyester according to claim 8, in which the ester residues comprise those of a steroid alcohol.

15. A polyester according to claim 14 in which the ester residues comprise those of cholesterol.

16. A polyester according to claim 8 in which the ester residues comprise those of a ($C_{1-20}$) alkanol.

17. A polyester according to claim 1 with a number of 5 to 1000 alkylene carbonic acid ester units.

18. A polyester according to claim 5, in which the carboxylic acid ester residues comprise a hydroxy carboxylic acid or its derivative.

19. A polyester according to claim 18 in which the carboxylic acid ester residues comprise those of lactoyl or glycol.

20. A polyester according to claim 5, in which the carboxylic acid ester residues comprise polylactoyl, polylactoyl-co-glycol or polyglycol, the and replace with "wherein the lengths of the chains are selected to function in avoiding formation by the polyester of a hydrogel".

21. A polyester according to claim 8, in which the carbonic acid ester residues comprise a carbamic acid ester derivative.

22. A polyester according to claim 5, 8 or 21 in which the ester groups are selected from the group consisting amino acid and peptide residues.

23. A polyester according to any one of claim 1–11 or 13–21, in which at least one of the terminal groups is a lipophilic residue.

24. A polyester according to claim 23 in which the lipophilic residue is a stearoyl group.

25. A pharmaceutical composition comprising a polyester according to any one of claim 1–11 or 13–21 mixed with a drug compound.

26. A pharmaceutical composition according to claim 25 comprising the polyester as a solid matrix for the drug compound.

27. A pharmaceutical composition according to claim 25 in microparticle or implant form.

28. A pharmaceutical composition comprising: a drug compound; and a biodegradable and biocompatible polyester, mixed with the drug compound, the polyester having linear ($C_{3-10}$) alkylene carbonic acid ester units in a homopolyester arrangement.

29. A pharmaceutical composition comprising: a drug compound; and a biodegradable and biocompatible polyester, mixed with the drug compound, the polyester having linear ($C_{3-10}$) alkylene carbonic acid ester units with cholesterol residues.

30. A pharmaceutical composition comprising: a drug compound; and a biodegradable and a biocompatible polyester, mixed with the drug compound, the polyester having linear ($C_{3-10}$) alkylene carbonic acid ester units having residues of a saturated or unsaturated ($C_{2-20}$) fatty acid.

* * * * *